US011456063B2

(12) United States Patent
Al-Faraje

(10) Patent No.: US 11,456,063 B2
(45) Date of Patent: Sep. 27, 2022

(54) DENTAL PATIENT MANAGEMENT SYSTEM

(71) Applicant: Novadontics, LLC, San Diego, CA (US)

(72) Inventor: Louie Al-Faraje, San Diego, CA (US)

(73) Assignee: Novadontics LLC, San Diego, CA (US)

( * ) Notice: Subject to any disclaimer, the term of this patent is extended or adjusted under 35 U.S.C. 154(b) by 199 days.

(21) Appl. No.: 16/563,894

(22) Filed: Sep. 8, 2019

(65) Prior Publication Data

US 2021/0074391 A1 Mar. 11, 2021

(51) Int. Cl.
*G16H 10/60* (2018.01)
*G16H 30/20* (2018.01)
*G16H 40/20* (2018.01)
*A61C 7/00* (2006.01)

(52) U.S. Cl.
CPC ............ *G16H 10/60* (2018.01); *A61C 7/002* (2013.01); *G16H 30/20* (2018.01); *G16H 40/20* (2018.01)

(58) Field of Classification Search
CPC ........ G16H 10/60; G16H 30/20; G16H 40/20; G16H 15/00; G16H 20/40; A61C 7/002; G06Q 50/22
See application file for complete search history.

(56) References Cited

U.S. PATENT DOCUMENTS

| 5,616,899 | A | 4/1997 | Recigno |
| 7,156,655 | B2 | 1/2007 | Sachdeva et al. |
| 7,966,269 | B2 | 6/2011 | Bauer et al. |
| 7,995,822 | B2 | 8/2011 | Lang et al. |
| 8,021,147 | B2 | 9/2011 | Sporbert et al. |
| 8,359,114 | B2 | 1/2013 | Steingart et al. |
| 8,465,280 | B2 | 6/2013 | Sachdeva et al. |
| 9,510,918 | B2 | 12/2016 | Sanchez |
| 2007/0167687 | A1 | 7/2007 | Bertolero et al. |
| 2007/0239488 | A1 | 10/2007 | DeRosso |
| 2007/0255589 | A1* | 11/2007 | Rodriguez ............ G16H 50/50 705/2 |

(Continued)

FOREIGN PATENT DOCUMENTS

| EP | 1262902 A1 * | 12/2002 | ............ G16H 70/20 |
| EP | 3131030 A1 | 2/2017 | |

(Continued)

OTHER PUBLICATIONS

Thyvalikakath, Designing Clinical Data Presentation Using Cognitive Task Analysis Methods, 2012, ProQuest LLC, pp. 1-265. (Year: 2012).*

*Primary Examiner* — Christopher L Gilligan
(74) *Attorney, Agent, or Firm* — Pablo Meles

(57) ABSTRACT

A dental implant management system includes one or more processors operationally coupled to one or more computer storage mediums where the one or more processors causes the one or more processors to perform the operations of presenting a user interface having a plurality of tasks for completion, presenting a plurality of guided checklists for the dental implant process, inputting values for one or more of blood pressure, heart rate, blood oximetry, medical conditions, or allergies, and using artificial intelligence to modify the checklist based on previous data entered. In one embodiment, a listing of tasks is color coded for a status regarding each of the plurality of tasks. Other embodiments are disclosed.

20 Claims, 16 Drawing Sheets

(56) References Cited

U.S. PATENT DOCUMENTS

| | | | |
|---|---|---|---|
| 2009/0198514 A1* | 8/2009 | Rhodes | G16H 10/60 705/3 |
| 2011/0008751 A1* | 1/2011 | Pettersson | A61C 5/77 433/167 |
| 2012/0065985 A1* | 3/2012 | Royal | G16H 10/60 705/2 |
| 2014/0046692 A1 | 2/2014 | Minter et al. | |
| 2014/0081659 A1 | 3/2014 | Nawana et al. | |
| 2014/0204190 A1 | 7/2014 | Rosenblatt, III et al. | |
| 2015/0019252 A1* | 1/2015 | Dawson | G06Q 10/10 705/3 |
| 2015/0320320 A1* | 11/2015 | Kopelman | G06T 7/55 433/24 |
| 2017/0360508 A1 | 12/2017 | Germain et al. | |
| 2020/0066391 A1* | 2/2020 | Sachdeva | A61C 5/30 |
| 2020/0100724 A1* | 4/2020 | Golay | G16H 70/60 |

FOREIGN PATENT DOCUMENTS

| | | | |
|---|---|---|---|
| WO | 2003019422 A1 | 3/2003 | |
| WO | 2006031096 A1 | 3/2006 | |
| WO | WO-2014004976 A1 * | 1/2014 | A61B 34/25 |

* cited by examiner

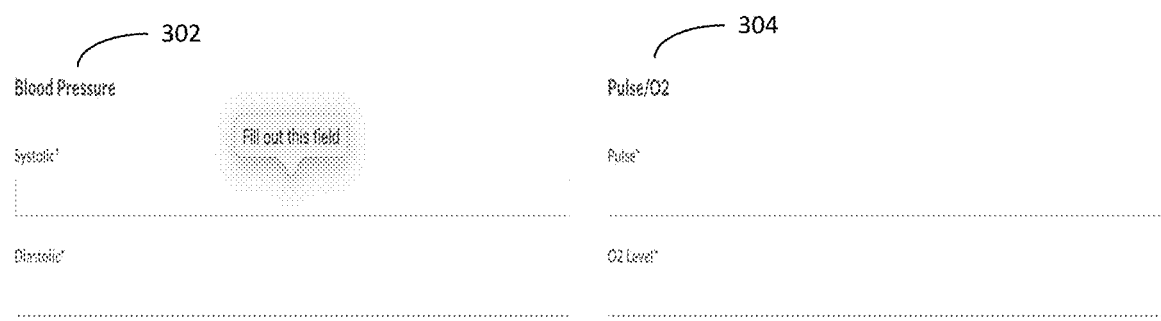
FIG. 13  300

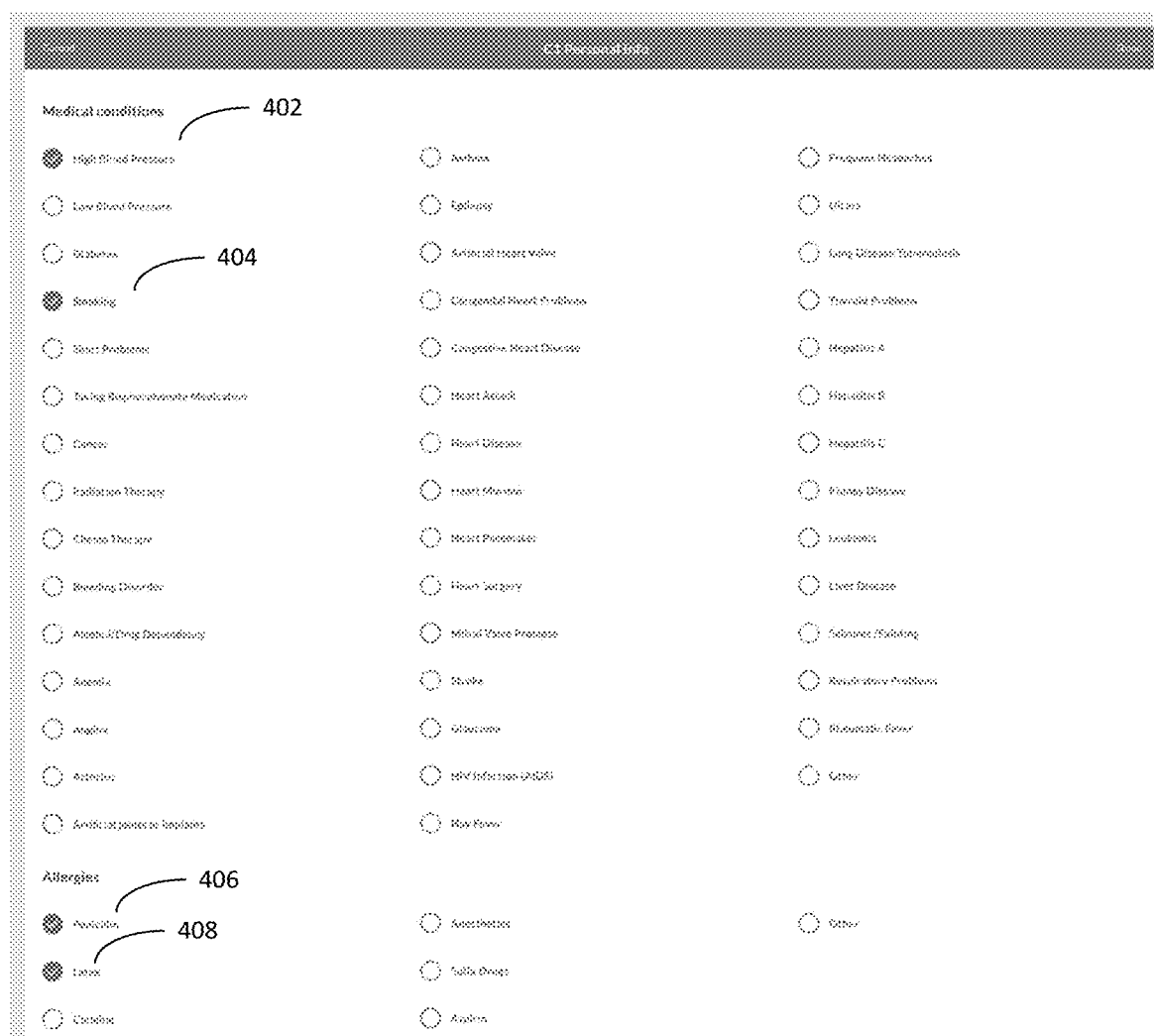
FIG. 14    400
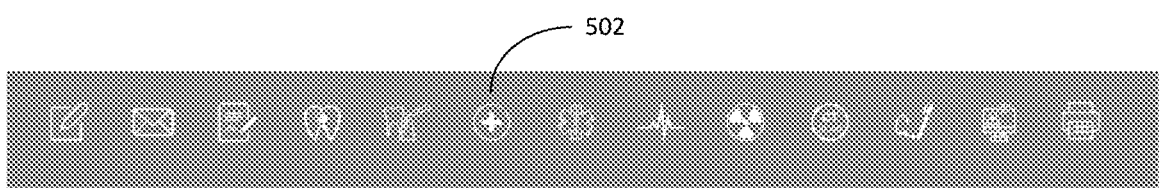
FIG. 15    500
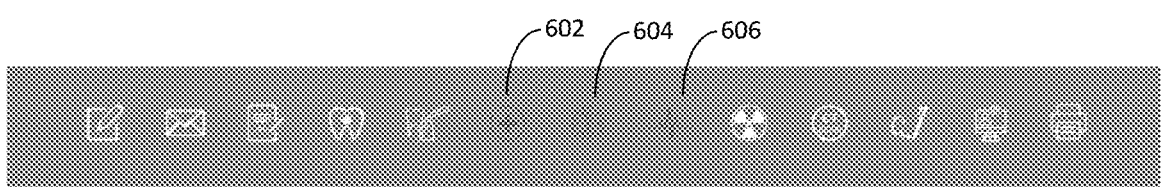
FIG. 16    500

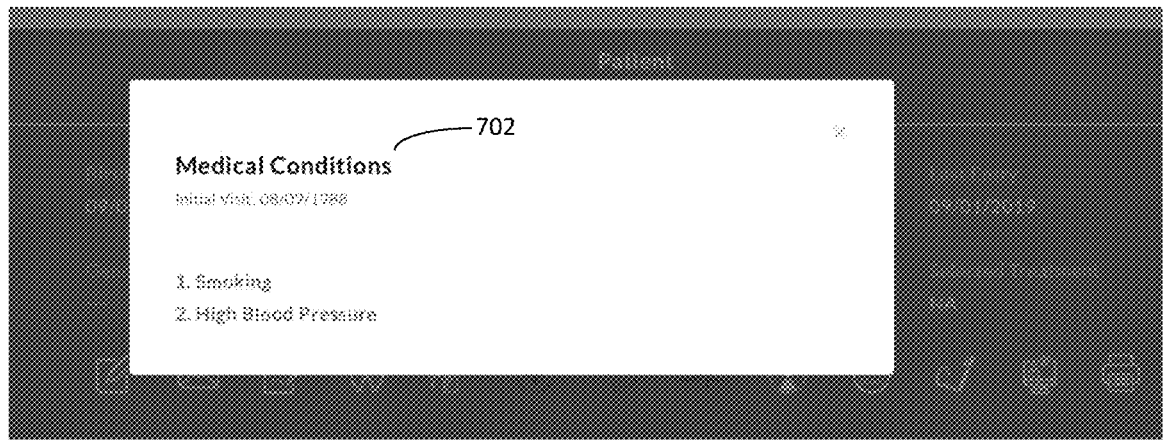
FIG. 17    700
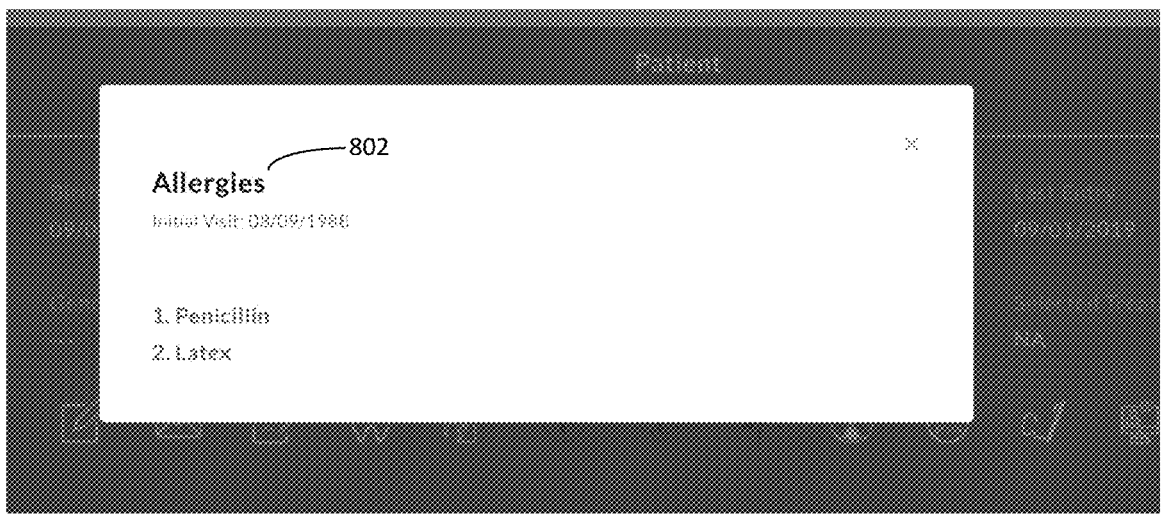
FIG. 18    800

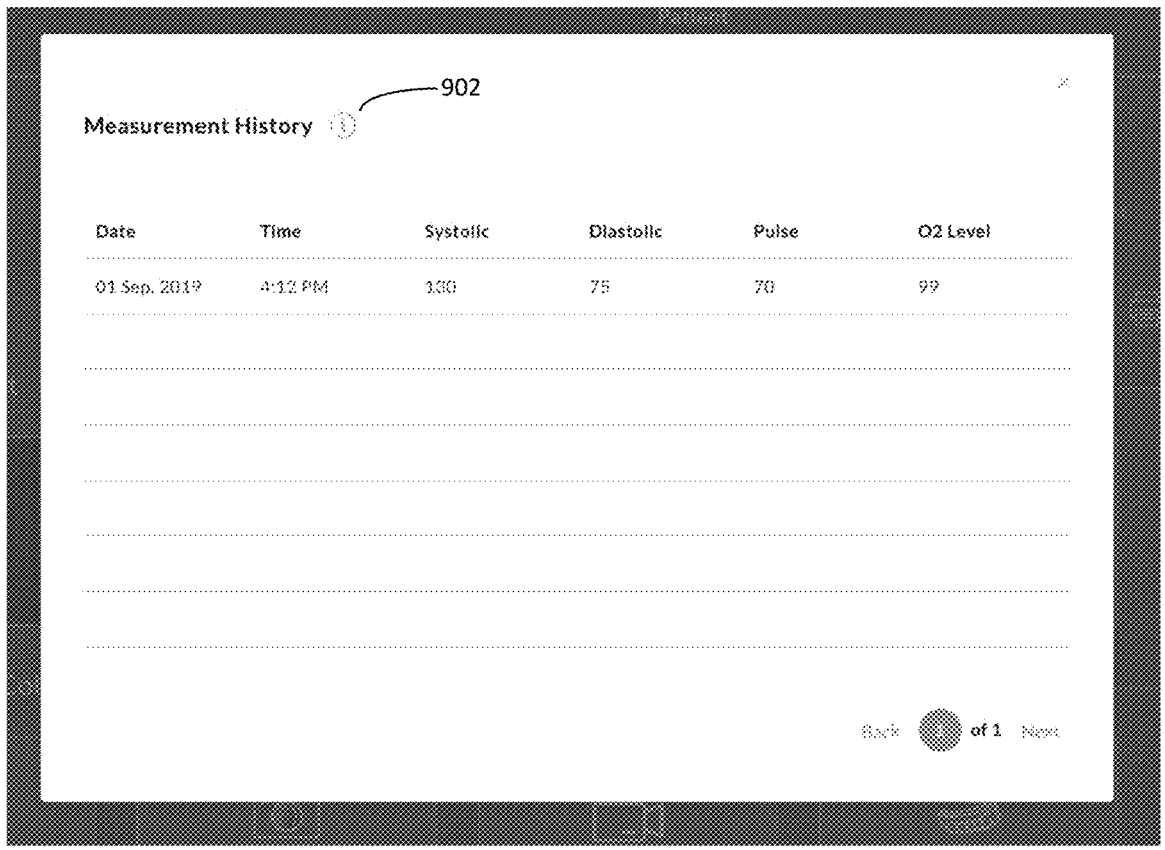
FIG. 19    900
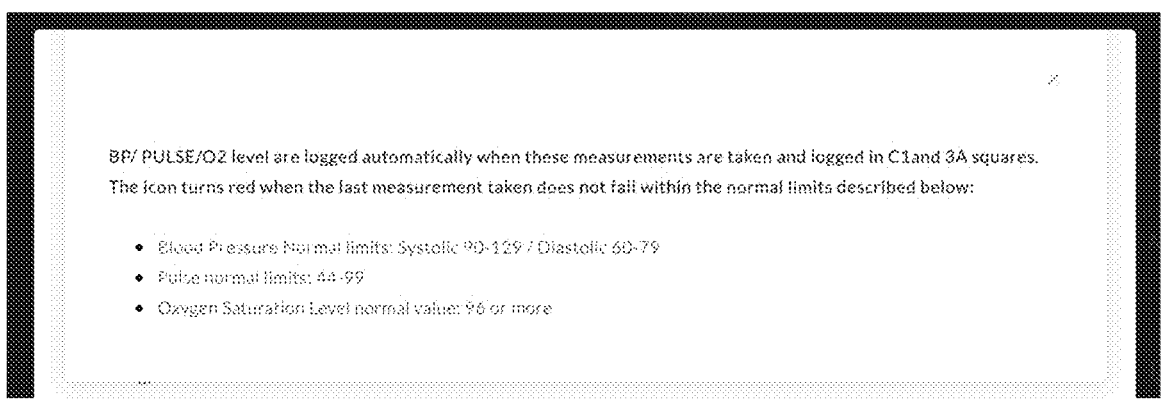
FIG. 20    950

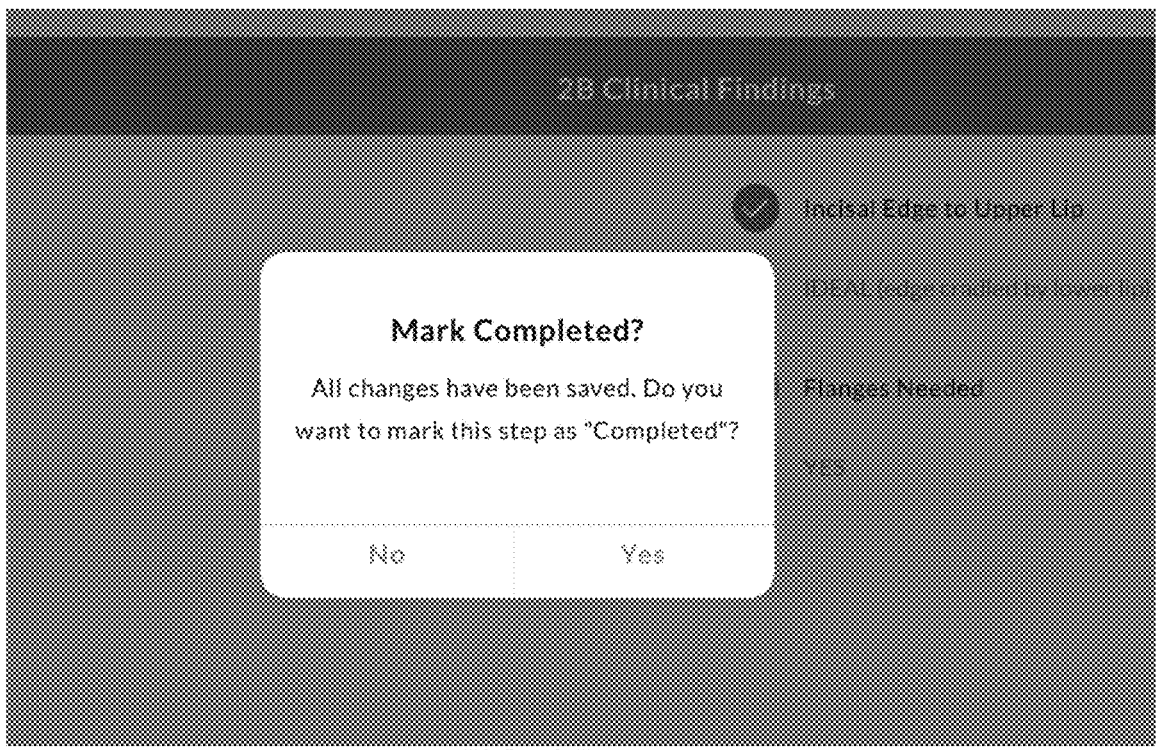
FIG. 25    1005
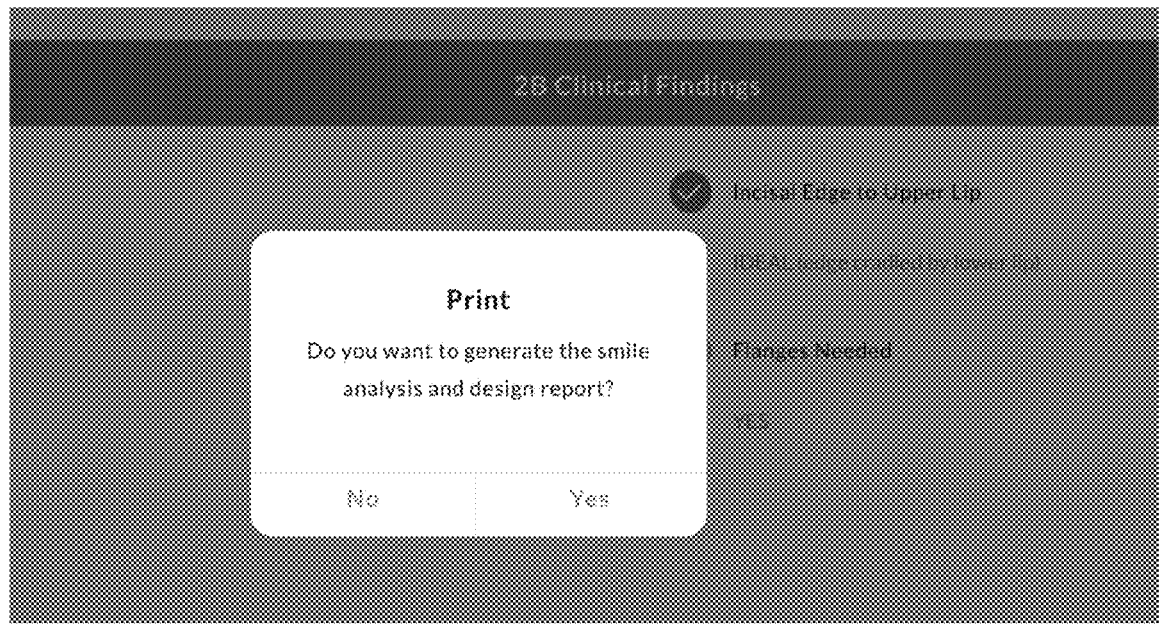
FIG. 26    1006
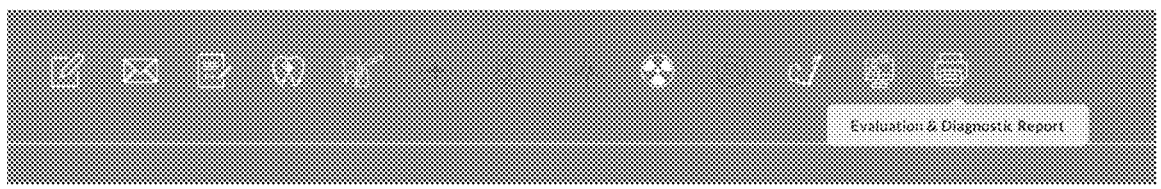
FIG. 27    1007

Smile Analysis and Design Report

Patient ID: 175
Initial Visit: August 2, 2019 12:00:00 AM GMT
Last Visit: September 2, 2019 1:10:30 PM GMT
Phone: 858.444.7688
Name: Dan
Email: info@implanteducation.net

| | |
|---|---|
| Symmetry: Horizontal lines are symmetrical (main occlusal plan matches inter-papillary line) | No |
| Symmetry: Vertical line perpendicular to the interpupillary line | No |
| Symmetry: Vertical line coincides with the dental midline | No |
| Symmetry: Vertical Teeth midline cant | No |
| Facial proportions: Mid face height equals lower face height | Yes |
| Facial proportions: Middle Face Larger | No |
| Facial proportions: Lower Face Larger | No |
| Lip characteristics: Upper Lip Length | |
| Lip characteristics: Upper Lip Horizontal Line in Mid Upper Lip | |
| Lip characteristics: Thickness of the upper lip | |
| Shape of face: Rectangle | No |
| Shape of face: Square | Yes |
| Shape of face: Oval | No |
| Shape of face: Triangle | No |
| Shape of face: Round | No |
| Facial profile type: Normal / Flat | No |
| Facial profile type: Convex | No |
| Facial profile type: Concave | No |
| Nasolabial angle (lip support): Normal (between 85-105 degrees) | No |
| Nasolabial angle (lip support): Inadequate (over 105) | No |
| Nasolabial angle (lip support): Excessive (under 85 degrees) | Yes |
| Vertical dimensions: Normal | No |
| Vertical dimensions: Decreased | No |

FIG. 28  1008

Evaluation & Diagnostic Report

Patient ID: JD480
Initial Visit: August 13, 2019 12:00:00 AM GMT
Last Visit: September 2, 2019 1:27:16 PM GMT
Phone: 123456789
Name: john
Email: JohnDoe@gmail.com

Consultation Visit

C1 Personal Info

| | |
|---|---|
| First Name* | john |
| Last Name* | Doe |
| Initial Visit Date (MM/DD/YYYY)* | 08/13/2019 |
| Cell phone number* | 123456789 |
| Patient's chief complaint* | Pain |
| Address (Street, City, State, Zip, Country)* | 4710 Ruffner Street, Suite B San Diego CA 92111 |
| Photo of the patient | No pictures taken. |
| How did you hear of us? | |
| M | K |
| Patient ID / Chart Number* | JD480 |
| Birthdate (MM/DD/YYYY)* | 07/08/1967 |
| Dental Insurance Carrier | Delta |
| Treatment Goal | Fixed teeth |
| Email* | JohnDoe@gmail.com |
| Gender | male |
| Medical conditions: High Blood Pressure | Yes |
| Medical conditions: Low Blood Pressure | No |
| Medical conditions: Diabetes | No |
| Medical conditions: Smoking | No |
| Medical conditions: Sinus Problems | No |
| Medical conditions: Taking Bisphosphonate Medication | No |
| Medical conditions: Cancer | No |

FIG. 29       1009

DENTAL PATIENT MANAGEMENT SYSTEM

FIELD OF THE DISCLOSURE

The present disclosure is generally related to systems for managing the process of treating dental patients, and more particularly to a dental patient management system such as a dental implant patient management system.

BACKGROUND

Practice management systems generally include the storage, retrieval, analysis, and transmittal of patient records, as well as the scheduling and billing for associated appointments, diagnoses, and treatments. Some practice management systems provide such capabilities in a consolidated form, but traditionally many of these functions are performed by separate and disparate systems that ultimately cause inefficiency and potential inaccuracies into the provided overall system. Still further, even where consolidated or electronic form practice management systems are provided, the communication of diagnosis and treatment data remains less than ideal. For example, consider that the key to treatment and quality results in the field of orthodontics is the proper placement and manipulation of a variety of elements (e.g., brackets, elastics, arch-wires, implants, abutments, prosthesis, and the like) upon a patient's teeth over numerous patient visits. Tracking the steps and results for a single patient is a challenge and for an entire practice further complicates matters.

Treatment can be tracked and recorded on standard two-dimensional tooth charts that are not always intuitive to orthodontists and their staff. The standard tooth chart is also disadvantageous when used to explain the diagnosis and treatment plan to a patient and/or the patient's parent or guardian not to mention the tracking of materials associated with a particular treatment plan.

BRIEF DESCRIPTION OF DRAWINGS

FIG. 13 illustrates an example of the system collecting blood pressure, and pulse and the oxygen saturation level values during a patient's first visit to establish a baseline for these values in accordance with the embodiments;

FIG. 14 is a representation of the user interface used when selecting any medical conditions or allergies during data collection in accordance with the embodiments;

FIGS. 15 and 16 are representations of the related icons associated with the user interface of FIG. 14 in the patient chart view which will visually change to enable a user to quickly see at a glance the conditions or allergies a patient has in accordance with the embodiments;

FIG. 17 is a user interface or pop-up menu of the medical conditions associated with the patient chart view of FIG. 14 and with the related icons of FIG. 16 in accordance with the embodiments;

FIG. 18 is a user interface or pop-up menu of the allergies associated with the patient chart view of FIG. 14 and with the related icons of FIG. 16 in accordance with the embodiments;

FIG. 19 is another user interface or pop-up screen enabling a user to access a history of measurements or data associated with an activated icon (from FIG. 16) such as blood pressure/pulse/blood oxygenation along with dates and times of recordation in accordance with the embodiments;

FIG. 20 is a user interface or pop-up screen that appears when activating or clicking on the circle-I icon in FIG. 19 where a user can view additional information and guidelines of what is considered normal values ranges for blood pressure/pulse/blood oxygenation in accordance with the embodiments.

FIGS. 25 and 26 are additional user interface options enabling the generation of a smile analysis and design report in accordance with the embodiments;

FIG. 27 illustrates the related icons of FIGS. 15 and 16 associated with the patient chart view which also enable a user to generate and print an evaluation and diagnostic report in accordance with the embodiments;

FIG. 28 is a representative smile analysis and design report in accordance with the embodiments; and FIG. 29 is a representative evaluation and diagnostic report in accordance with the embodiments.

DETAILED DESCRIPTION

Existing dental and medical practice management software tools generally fall under the category of generic word-processing or spreadsheet tools such as Word or Excel where no intelligence and practical guidance for a given practice is provided.

Figure 1:
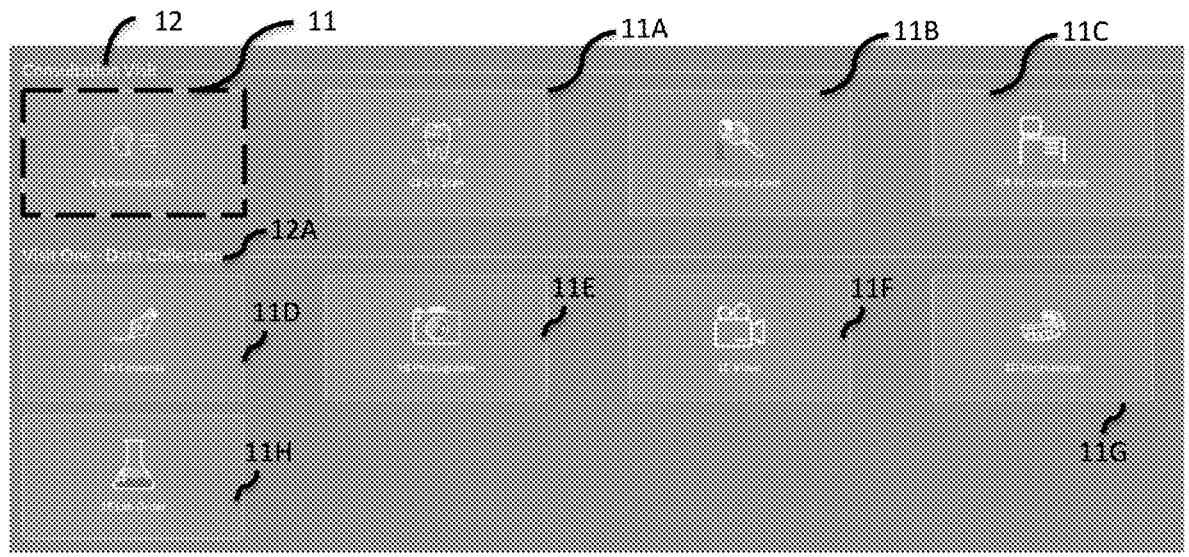
FIG. 1 is a representation of a user interface for a patient data collection, data analysis, and generating diagnostic data reports that can be used with the embodiments herein.

The blocks or squares (or steps) in the current embodiments can provide a guide for a dental implant (or dental and medical in general) treatment journey from personal and diagnostic data collection to prosthesis delivery. When following the squares (as shown in FIG. 1), the user performs a thorough state of the art data collection and data analysis that leads to safer and more predictable treatment. The system aspires to lift minimum standards of care in a particular practice to a gold standard of care or higher for a given practice. Each system in accordance with the embodiments can be designed with experts in a given field providing the appropriate data collection and treatment plans needed. In some embodiments, the system can evolve and gain intelligence as it is being used over time.

At a glance, the user can see where is a patient resides in the process of the treatment (darkened or highlighted square feature, for example) and in seconds the user can generate sophisticated evaluation and smile analysis reports for ease of communications with other health care professionals, dental labs, imaging centers, etc. as needed.

In most embodiments, if not all embodiments, no data would stored be stored on any client computer or mobile devices. All data would be stored securely on the cloud such as with AWS (Amazon Web Services). When entering any data or images in a patient file, the data would be stored on the cloud and made available on demand from any device with the proper login and password. Of course, in certain instances, embodiments within contemplation of the claims can have data stored securely on client computers or mobile devices as allowed and recommended by prevalent standards.

As required, detailed embodiments of the present disclosure are disclosed herein, however, it is to be understood that the disclosed embodiments are merely examples of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure and function. Further, the terms and phrases used herein are not intended to be limiting; but rather, to provide an understandable description of the disclosure.

According to various embodiments of the present disclosure, disclosed is a system and method for a dental patient management system such as a dental implant patient management system using one or more user interfaces, client devices and server or cloud devices. The embodiments utilize the actual experience of an dental practice to implement an efficient overall system that is best suited for best patient outcomes and practice management.

More specifically, referring to user interface 10 of FIG. 1, a dental implant patient management system can provide a comprehensive and tailored or customized interface that breaks down all the steps necessary to efficiently run a dental practice. Although the examples provided are specifically directed towards a practice that performs dental implants, the embodiments herein can be adapted to any dental practice or even any other medical practice particularly where materials are needed to provide the patient health services. For example, any surgical practice such as an orthopedic surgeon, podiatrist, or ophthalmologist can adapt and utilize the methods and systems as contemplated herein as a framework for data entry.

The embodiments herein provide at least three (3) distinctive features that help mainstream the treatment protocol in a dental office which can significantly reduce potential errors and complications leading to greater patient satisfaction and greater profitability in such dental practice.

A first feature as illustrated in FIG. 1, is a user interface 10 that breaks down the initial patient interactions into visits 12 and 12A and steps 11, 11A-11H within each visit. The patient treatment journey in the dental office can be divided into a specific number of visits and each visit having certain steps. The user interface 10 can be customized to have any number of steps within a particular visit or customized to rearrange certain steps for a different order on a same visit or a different visit. Although certain steps are ideally suited for certain visits and some embodiments will have a default arrangement based on a customary and typical board certified practice, the embodiments are not limited to the particular visits and steps illustrated. Some steps may have some chronological flexibility whereas others may not. In this particular embodiment, an initial visit or consultation visit 12 can include a step 11 for collecting patient personal information. When any step is completed, the related square becomes visually distinguishable from the uncompleted steps. For example, the square for the completed step turns dark indicating the completion of the step. Step 11 is darkened or highlighted or otherwise made visually distinguishable as being completed as shown in FIG. 1.

The "darkening" or "highlighting" can be any visual indication that differentiates the other uncompleted steps from the completed steps. Darkening or highlighting can include using a color scheme that shows a particular step as being completed. For example, a green highlighted box or icon can indicate a completed step or task and a red highlighted box or icon can indicate an incomplete step. In another embodiment, a green highlight can indicate a completed step or task, a yellow highlight can indicate a step or task under progress, and a red highlight can indicate an incomplete or a yet-to-be started step or task. In the example shown, the steps 11A (CT scan), 11B (Clinical Exam), and 11C (Transfer to Coordinator) are shown as part of an initial consultation visit 12 and steps 11D (Consents), 11E (photographs), 11F (video), 11G (Impressions), and 11H (Lab Orders) are part of a second visit 12A which can be entitled "Data Collection". Other visits can be divided as desired with a number of steps. Such others visits could be entitled, for example, as "Data Analysis", "Surgical Treatment", and "Prosthodontic Treatment."

As noted above, each visit can include a specific number of steps (corresponding to the squares or rectangles or desired shapes enumerated as 11-11H). When the tasks of each visit are performed, the color of the can square can change. The visual change helps the entire dental team know where the patient is located in the treatment journey at a glance. In other words, the status of the patient and the progress in their treatment plan is readily apparent from the user interface.

Figure 2:
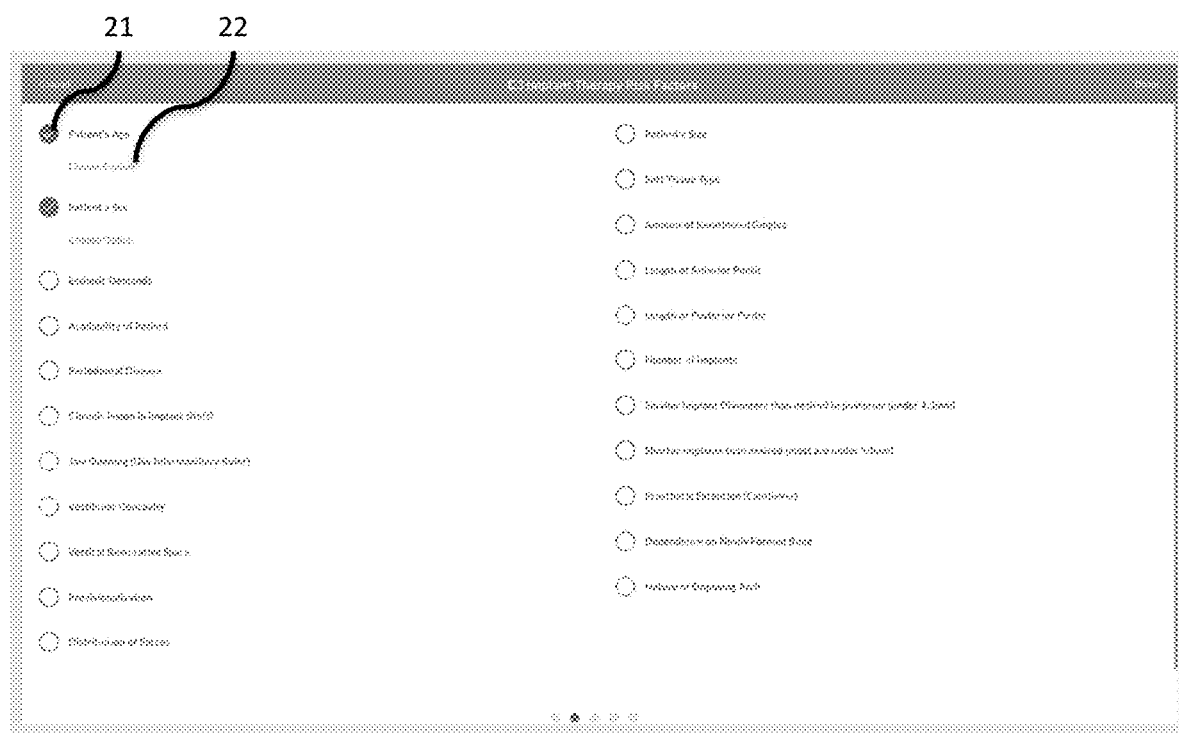
FIG. 2 is a representation of a user interface using smart checklists in accordance with the embodiments.

Unlike paper format checklists, the electronic checklists (as a result of activation of any of the squares 11-11H) provide several important propriety features. In one aspect, the embodiments can include color-coded or visually distinguishable Checkboxes. When marked, the checkboxes change colors or provide some other visual queue signaling the relative conditions in the checklist for the patient. For example, when the user activates box 11B (Clinical Exam), a user interface 20 propagates on a client device such as a laptop or notepad device as shown in FIG. 2.

In the context of the embodiments herein, a Smart checklist can mean a list having any combination of the following features: 1. Providing color-enabled checkboxes for the items on the checklist when selected; 2. For most checkboxes, providing choices to select from (and thus providing all possible answers for the data to be collected through the checklist (see FIGS. 3 & 7); 3. The ability to write a note if none of the choices provided are what the user is seeking as an input (see FIG. 6); and 4. For many checkboxes, more information or an explanation readily available by activating or clicking on the "circle-I" icon (see FIGS. 4 & 5).

Figure 3:
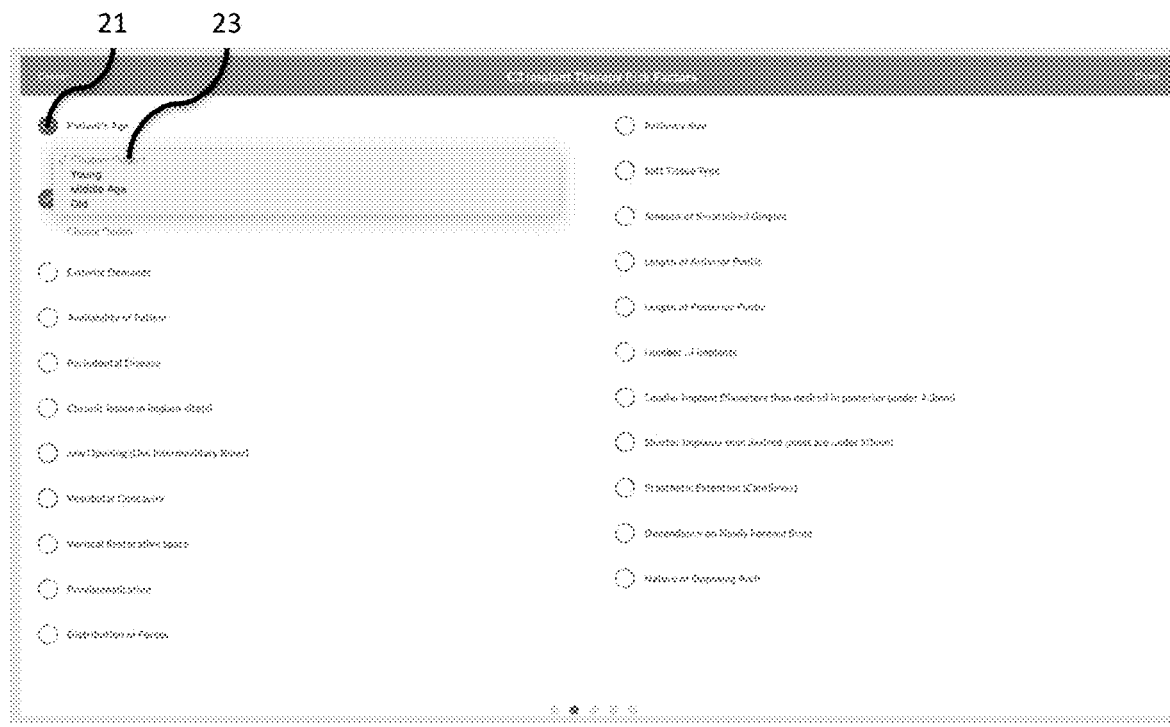
FIG. 3 is a further representation of the user interface of FIG. 2 further providing answer options in accordance with the embodiments.

The clinical exam 11B can include a plurality of checklist items 21 for the practitioner or office staff to complete for each patient. If there is no manual entry, there can be an answer option 22 that can be selected to help the dentist or staff with all the possible answers. In FIG. 3, a query for a patient's age corresponding to checklist item 21 can include a pull-down menu of ages or age ranges or a manual entry of text or if exact age is not critical, then a descriptor such as "young", "middle age" or "old" can be selected as part of a pull-down menu 23 as shown in FIG. 3 when activating the answer options feature (22 shown in FIG. 2) or by placing a cursor over the answer options feature 22. In some embodiments, the drop down menu requires the selection of one of the choices provided and in yet other embodiments, when the choices requires additional flexibility for an input, then the user interface can provide an open-ended option such as "Other, see notes" or "Other, enter notes" as an option to enable the user to type the answer that was not provided as an option. In some embodiments, when selecting or clicking on this open-ended choice, the user can get a box to write notes in the input box as needed.

Figure 4:
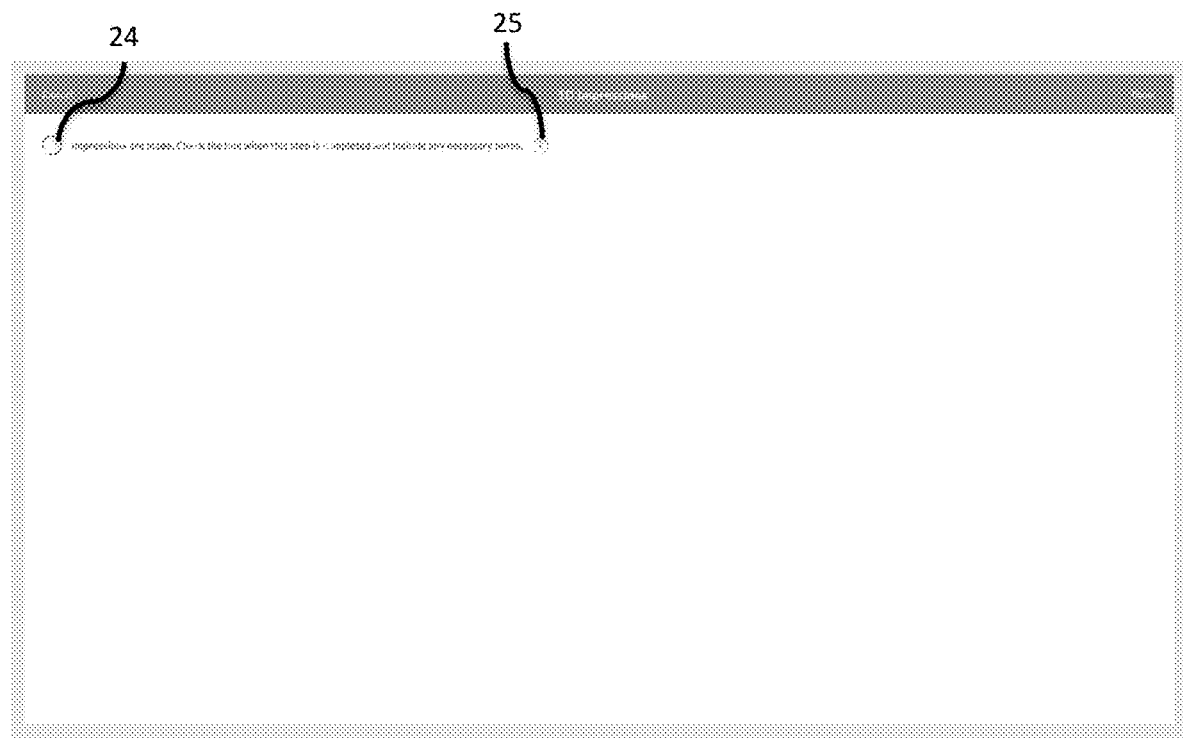
FIG. 4 is a representation of the user interface of FIG. 2 further providing on-demand information which is shown as being hidden in accordance with the embodiments.
Figure 5:
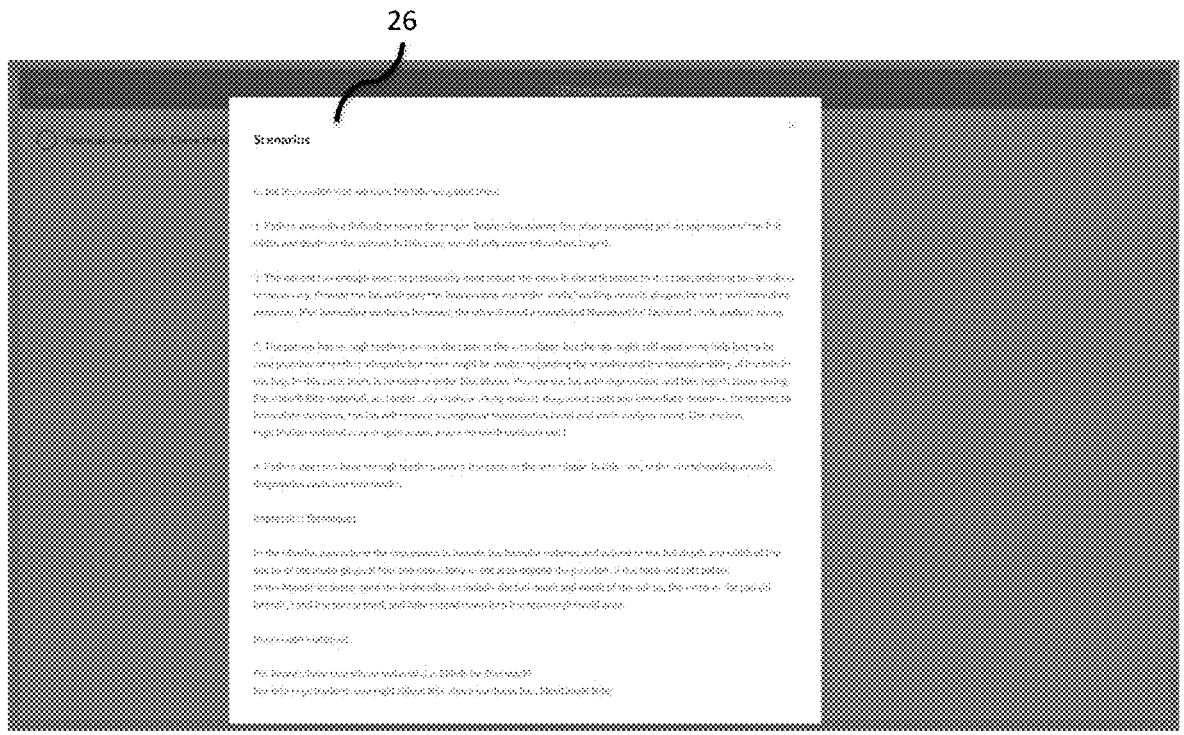
FIG. 5 is a representation of the user interface of FIG. 4 presenting the on-demand information upon user activation in accordance with the embodiments.
Figure 6:
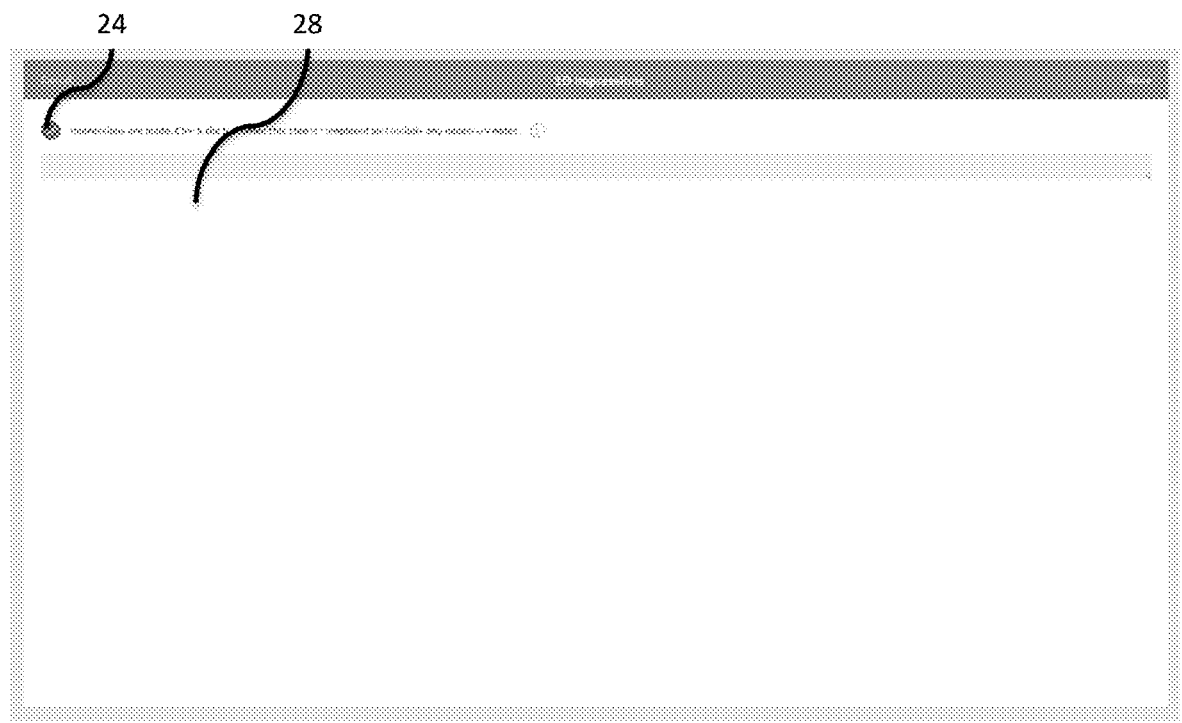
FIG. 6 is a representation of the user interface of FIG. 2 that provides an option to add text or notes in accordance with the embodiments.

FIG. 4 illustrates a user interface 30 that results when activating box 11G (Impressions) of FIG. 1. This illustrates an information feature 25 (shown as a "circle-I") for a particular checklist item 24. When the information feature 25 exists, the feature 25 can contain hidden available-on-demand useful information associated with the checklist item or associated with the selected box 11G (Impressions). FIG. 5 further illustrates the user interface 30 and the additional information 26 that is brought into view (as a pop-up window) when the user selects the information feature 25 of FIG. 4. In this instance, the additional information 26 describes various scenarios resulting from a visit when impressions (of a patient's teeth) are made. FIG. 6 further illustrates another aspect of the user interface 30, namely an area 28 allowing the dentist or their staff to enter text, notes, touch screen entries, images or any combination thereof if the client device is provisioned with such capability. The user can also check the checklist item 24 when the impressions are complete.

Figure 7:
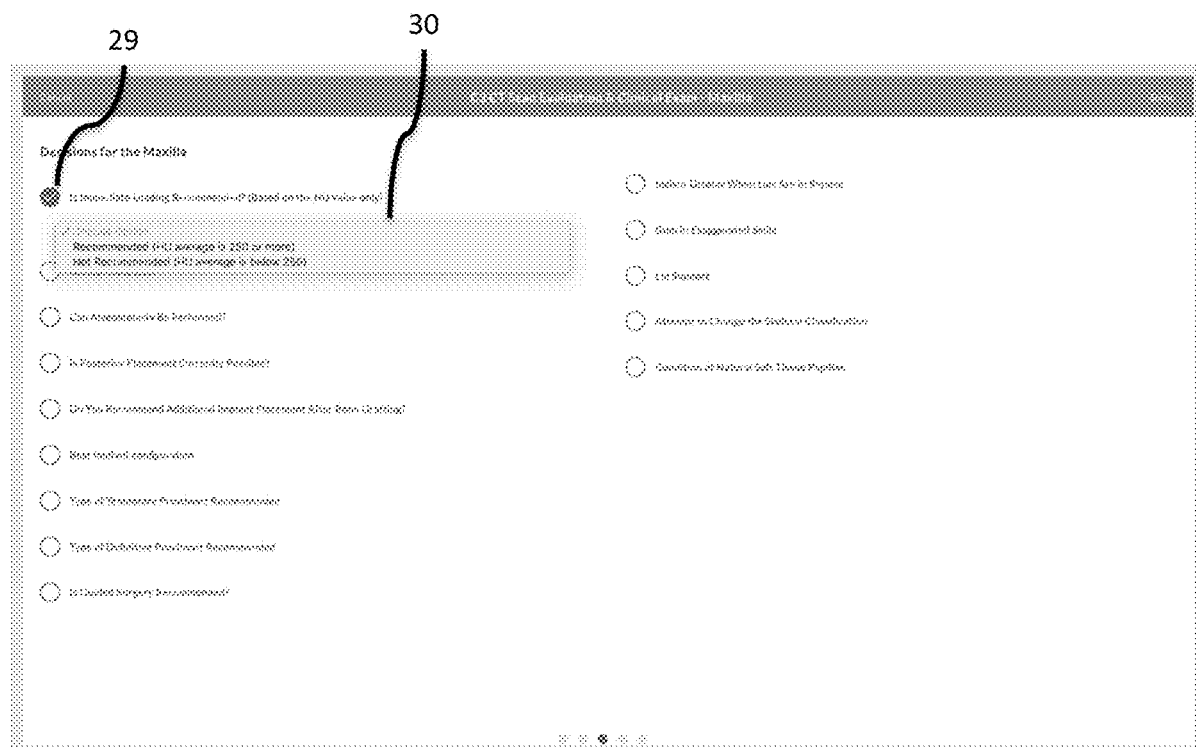
FIG. 7 is a representation of the user interface of FIG. 2 providing for options to recommend or eliminate treatments based on prior data entered in accordance with the embodiments.

Another user interface 40 of FIG. 7 illustrates suggestions or guidance 30 as recommendations or elimination of treatments that can be suggested by the system as a result of selecting a particular checklist item 29 (of the clinical exam 11B of FIG. 1) and further as a result of the prior answers chosen or data entered. In this instance, immediate loading of the maxilla can be determined based on bone density measurements that may have been entered into the system or otherwise observed by the dentist. Other recommendations or decision can be made in this manner using artificial intelligence based on the prior data entered into the system. As additional data is entered, the system can dynamically decide the further course of treatment based on a database of information.

Figure 8:
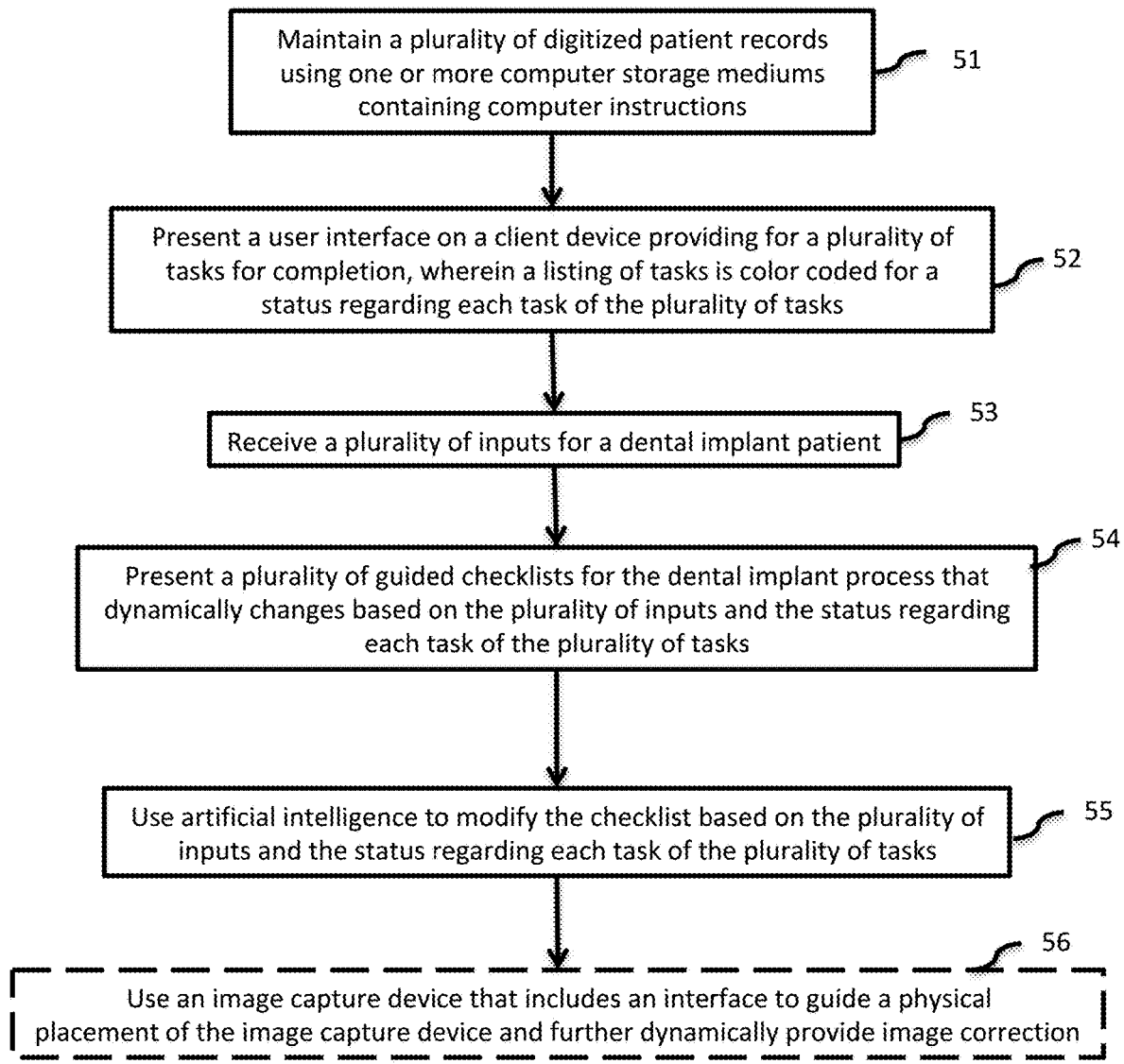
FIG. 8 is a flow chart of a method in accordance with the embodiments.

Referring to the flow chart of FIG. 8, a method 50 of managing a dental implant process can include the step 51 of maintaining a plurality of digitized patient records using one or more computer storage mediums containing computer instructions and the step 52 of presenting a user interface on a client device providing for a plurality of tasks for completion where a listing of tasks is color coded for a status regarding each task of the plurality of tasks. The method 50 can further include the step 53 of receiving a plurality of inputs for a dental implant patient, the step 54 of presenting a plurality of guided checklists for the dental implant process that dynamically changes based on the plurality of inputs and the status regarding each task of the plurality of tasks, and the step 55 of using artificial intelligence to modify the checklist based on the plurality of inputs and the status regarding each task of the plurality of tasks. In some embodiments, the method 50 can further include the step 56 of using an image capture device that includes an interface to guide a physical placement of the image capture device and that further dynamically provides image correction.

Figure 9:
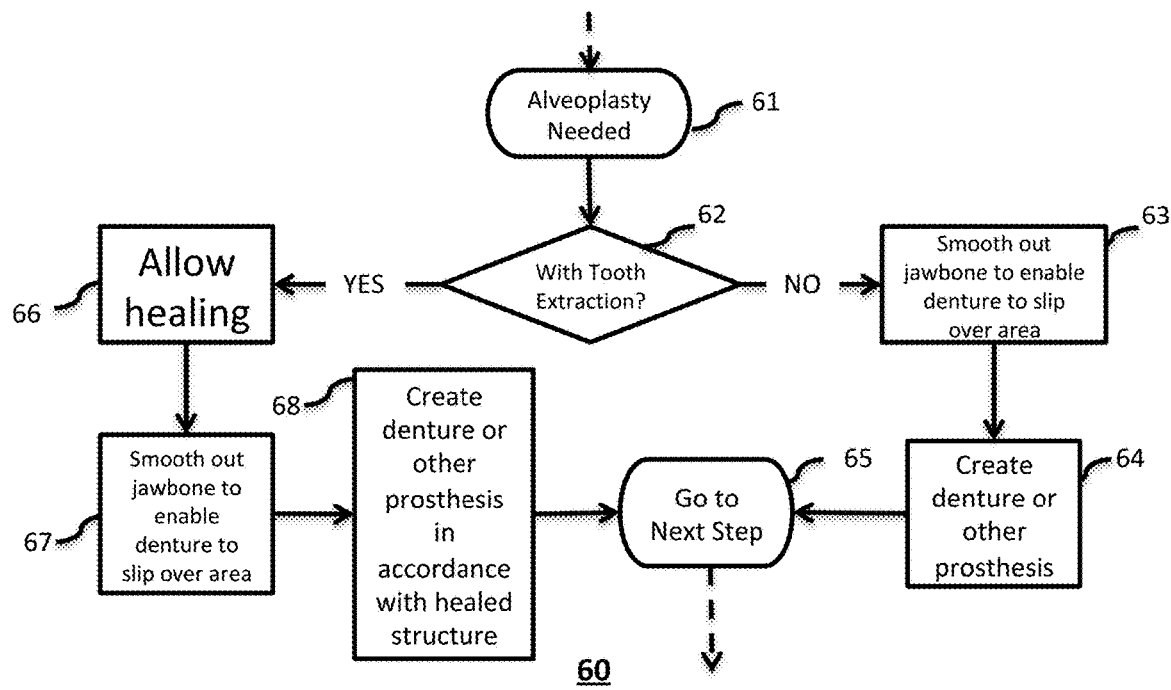
FIG. 9 is a flow chart of a method demonstrating the use of artificial intelligence in accordance with the embodiments.
Figure 10:
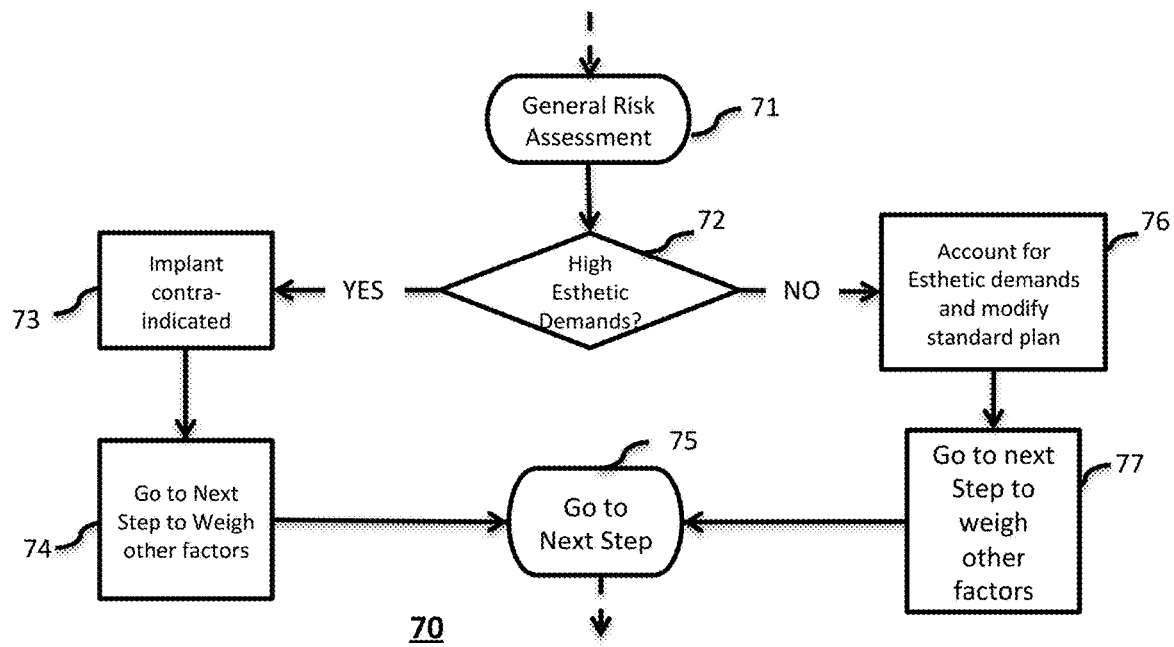
FIG. 10 is another flow chart demonstrating the use of artificial intelligence in accordance with the embodiments.

FIGS. 9 and 10 illustrates several flow charts of methods 60 and 70 that can utilize artificial intelligence to guide a practitioner through the dental implant process based on the current input provided to the system. In FIG. 9, the implant system determines that alveoplasty is needed at step 61 and make further necessary inquiries whether a tooth extraction is further needed in association with the alveoplasty at decision block 62. If no tooth extraction is involved, the practitioner can possibly proceed to smooth out the jawbone at step 63 to enable a smooth placement and/or removal of the denture or other prosthesis as contemplated by the treatment plan. Accordingly, the denture or other prosthesis is created at step 64 before allowing the dental implant process to move to the next step at step 65. If a tooth extraction is indicated at decision block 62, then the tooth is removed and sufficient time is provided to allow the patient to heal at step 66 before the jawbone is smoothed out at step 67. At step 68, a denture or other prosthesis is created in accordance with the healed bone structure before the dental implant process moves to the next step at step 65.

FIG. 10 illustrates just one aspect or consideration among many (as noted above) in the general risk assessment 71. In this method 70, a determination is made whether the patient has high esthetic demands beyond reason or practical considerations at decision block 72. If the patient does have high esthetic demands, then it can be considered as a weighting factor against proceeding with a dental implant at step 73. The practitioner can model or provide a heavy weighting factor or score for the particular patient with a score that exceeds a threshold that can end the implant process at that juncture or the model or score can allow the process to proceed with consideration of other factors as shown at step 74 before going to a next step. In some embodiments, the next step can be consideration of other factors like smoking habits, alcohol abuse, periodontal disease, or other considerations which all may be contra-indications for proceeding with an implant. Other indications can counter the contra-indication such as a lack of a smoking habit and good hygiene. If no high esthetic demands or an insufficiently high enough esthetic demand is found at decision block 72, then the dental implant system accounts for such esthetic demands and modifies the plan at step 76 from the standard plan. The method 70 can then proceed to weight other factors at step 77 before going to step 75.

Figure 11:
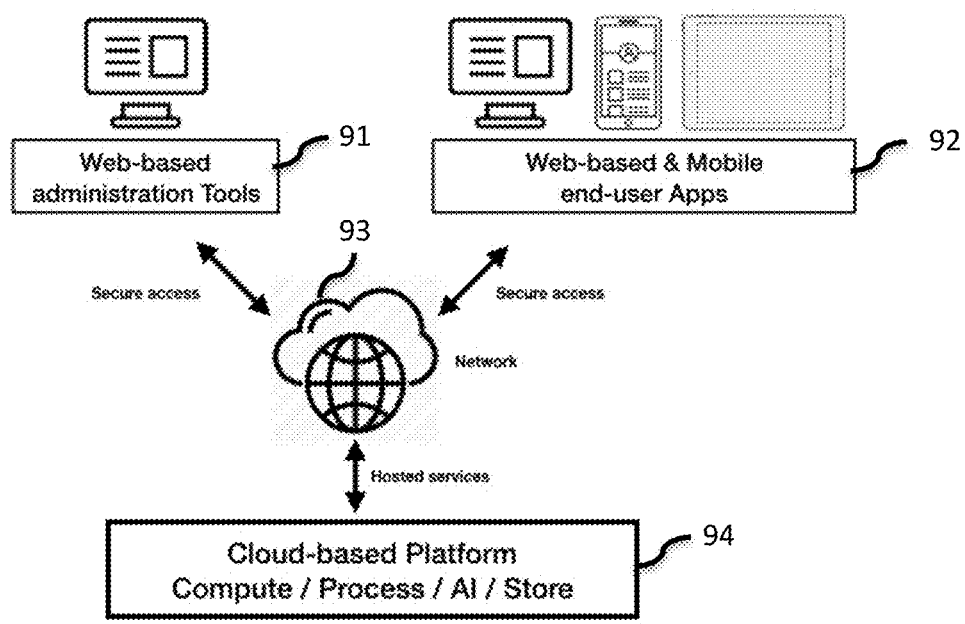
FIG. 11 is a block diagram of a system in accordance with the embodiments.

In some embodiments as further illustrated and described with respect to the system 90 of FIG. 11, a dental implant management system can include one or more coupled computer systems that can include a network 93 securely coupling a client device having web-based administration tools 91 and a number of client devices having web-based and mobile end-user based application coupled to cloud based platform 94 that provides hosted services such as computing, processing, artificial intelligence, and/or storage.

Figure 12:
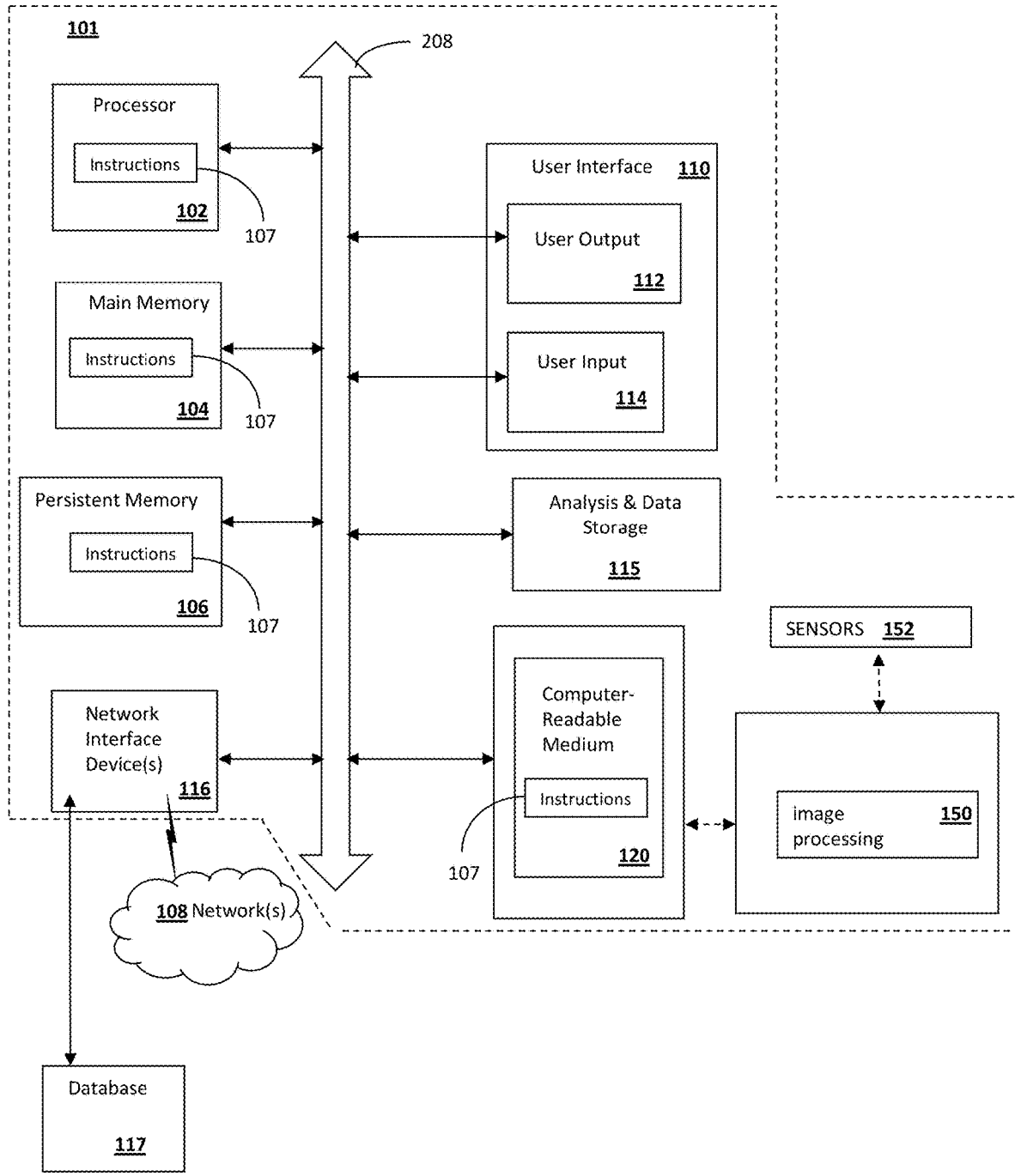
FIG. 12 is a block diagram of a system in accordance with the embodiments.

In some embodiments as further illustrated and described with respect to the system 200 of FIG. 12, a dental implant management system can include one or more computer storage mediums containing computer instructions and digitized patient records, one or more processors operationally coupled to the one or more computer storage mediums where the computer instructions when executed by the one or more processors causes the one or more processors to perform the operations of the method 50 described above. Namely, the one or more processors can present a user interface having a plurality of tasks for completion where a listing of tasks is color coded for a status regarding each of the plurality of tasks, present a plurality of guided checklists for the dental implant process, input values for one or more of blood pressure, heart rate, blood oximetry, medical conditions, or allergies, and use artificial intelligence to modify the checklist based on previous data entered. In some embodiments, the one or more processors are operationally coupled to storage mediums that are cloud based processors. In some embodiments, the storage mediums are cloud based and the system is configured for a multi-user environment enabling a plurality of registered users to interact with the system. In some embodiments, the plurality of guided checklists dynamically modifies based on inputted values and a current status of the dental implant process. The artificial intelligence (AI) utilized by the embodiments disclosed herein can elevate the standard of data collection (see FIG. 13, for example) and provides AI features throughout the process of patient diagnostic data collection and data analysis.

In one embodiment, the checklist or guided checklist can include one or more of the following that can be categorized or sub-categorized as part of diagnostic data collection, risk factors including general risk factors, esthetic risk factors, functional risk factors, occlusal risk factors, or biomechanical risk factors. The diagnostic data collection can include both subjective and objective information about the patient such as the patient's chief complaint, the patient's goals and desires, health history, dental history, current and previous medications, allergies, bisphosphonate treatment including type and amount of time on medication, full mouth radiographs, panoramic radiographs, periodontal charting, status of existing restorations and etiology of any missing teeth, caries, or fractures. The diagnostic data collection can further include a TMJ evaluation, an occlusion evaluation, a soft tissue evaluation (biotype and adequacy of attached keratinized gingiva), an oral cancer screening, and photographs such as a full face, full face with smile, frontal and lateral views with retractors with teeth closed and slightly apart, and occlusal views. The diagnostic data collection can also include impression and bite registration or facebow which will be sent to the lab for fabrication of diagnostic casts, a diagnostic wax-up, and a radiographic template. The diagnostic data collection further include tooth shading, shape and size of planned teeth, referral to imaging lab for CT scan, and conversion of raw CT data to SimPlant (Materialise) or Procera (Nobel Biocare) software protocols if guided surgery is desired.

As noted above, the checklist can further assess the general risk factors for a particular patient. Note that the presence of one risk factor is not necessarily a contraindication to implant treatment. However, the presence of several risk factors can represent a high-risk situation or a contraindication to treatment in some instances. The general risk factors can include a very young age or a very old age, a compromised medical condition, a compromised psychological condition, high esthetic demands, limited availability for treatment and maintenance appointments, smoking habits, alcohol abuse, temporomandibular disorder, periodontal disease, etiology of edentulism, small jaw opening, poor hygiene, poor bone density, vestibular concavity or ridge dimensions, vertical bone resorption, reduced vertical distance between bone crest and opposing tooth, mesiodistal dimensions of the edentulous space, acute lesions, chronic lesions distant from the prospective implant site, or bony lesions.

With respect to esthetic risk factors, the checklist can also include one or more factors of high maxillary gingival smile line, low mandibular gingival smile line, scalloped gingiva (high possibility of recession), thin gingiva (high possibility of recession), papillae of adjacent teeth (if thick and short, then "natural regeneration" of the papillae adjacent to the planned implant restoration is facilitated and if long and thin, then complete regeneration is difficult to achieve), form of natural teeth (where it is easier to achieve good esthetics with square-shaped teeth than it is with triangular teeth because of the form or architecture of the soft tissue around the triangular teeth), shape of interdental contact (where the larger the interdental contact surface, the smaller the apillary space and the simpler the papillary regeneration), the position of interdental contact (if the contact is less than 5 mm from the bone margin, regeneration of the papilla takes place in practically all cases, but the chances decrease as the distance increases), the vestibular concavity, the existence of adjacent implant (where it would be difficult to achieve papillary regeneration between two implants because of the absence of a bony papilla (septum) in that situation), vertical bone resorption (which would lead to deep implant placement, unless bone grafting is performed, and to more difficult papillary regeneration), proximal bony leaks (if the proximal bony papillae are absent, soft tissue papillary regeneration will be difficult to achieve), high esthetic requirements, or unstable provisional restoration.

With respect to functional risk factors, the checklist can include one or more factors of bruxism, clenching, tongue thrusting, large tongue size, type of diet, posterior position of planned implant (where there can be higher stress levels in the posterior region), opposing arch (from more to less favorable, the scenarios are removable implant-supported prosthesis, natural teeth, and fixed implant-supported prosthesis), or optimal implant positioning (where improper positioning or angulation will lead to bone and soft tissue loss).

With respect to occlusal risk factors, the checklist can include one or more factors of unbalanced occlusion, presence of wear facets, posterior bite collapse, history of cracks and factures of natural teeth, direction of load (if the load on an implant is not directed toward its long axis, a variety of problems will occur, including component failure, prosthetic material failure, and bone loss due to overstresses in particular areas, among others), wide occlusal table, or lateral occlusal contact on the implant-supported prosthesis only.

With respect to biomechanical risk factors, the checklist can include one or more factors of the number of implants possible or desired less than the number of roots replaces, the small implant diameter, the short implant, the connection to natural teeth, unsplinted implant crowns, straight (not tripod) configuration, excessive number or size of pontics, use of cantilever design, implants offset from center of the prosthesis, excessively high restoration (unfavorable implant length-to-crown height ratio), unsatisfactory primary implant stability, lack of passive prosthetic fit, pier abutment, mandibular flexion, or immediate loading.

In some embodiments, the system can include an image capture device that includes an image capture user interface that guides in a physical placement of the image capture device and further dynamically provides image correction.

In yet some other embodiments, the dental implant management system uses a matrix based on the rules and statistics that define input parameters to maximize correction results or reduce risk of harm to a patient. In some embodiments the user interface further presents a divided calendar for patient visits including a consultation visit, a data collection visit, a data analysis visit, a surgical treatment visit, and a prosthodontics treatment visit. Each of the visits can include any number of tasks. For example the consultation visit can include a user interface that includes a module for inputting a patient's personal profile information. The consultation visit or the data collection visit can include a module for obtaining a patient's consent and other acknowledgements. The data collection visit can include a module for obtaining digitized imaging information selected among one or more of computer tomography images, photographs, video, x-rays, or magnetic resonance imaging. The data collection visit can also include a module for obtaining dental impressions. In some embodiments, the data collection visit can include use of a camera operationally coupled to one or more processors configured to guide and take pre-set images based on a desired smile profile for the patient.

In some embodiments the surgical treatment visit or the prosthodontics treatment visit can include a module for coordinating lab orders and maintaining inventory for materials used in a dental implant process.

In some embodiments of the dental implant management system, the system can be a client device having one or more computer storage mediums containing computer instructions enabling secure access to digitized patient records, one or more processors operationally coupled to the one or more computer storage mediums where the one or more processors perform the operations of presenting a user interface having a plurality of tasks for completion, wherein a listing of tasks is color coded for a status regarding each task of the plurality of tasks, presenting a plurality of guided checklists for the dental implant process, and receiving input values for one or more of blood pressure, heart rate, blood oximetry, medical conditions, or allergies. The client device can further use artificial intelligence to modify the checklist based on previous data entered. The client device can have one or more storage mediums that are operationally coupled to remote storage mediums and remote processors enabling remote storage and processing of data and further configured for a multi-user environment enabling a plurality of registered users to interact with the system. In some embodiments, the client device further can include an image capture device that includes an image capture user interface that guides in a physical placement of the image capture device and client device and further dynamically provides image correction. In some embodiments, the client device can include a module for obtaining either locally or remotely digitized imaging information selected among one or more of computer tomography images, photographs, video, x-rays, or magnetic resonance imaging. In some embodiments, the client device can include a user interface that includes a module for obtaining a patient's consent and other acknowledgements on a touch screen or on a biometric input device indicative of a patient's consent. In some embodiments, the user interface can further include a module for coordinating lab orders and maintaining inventory for materials used in a dental implant process.

In some embodiments, the system can further include a computer-storage media coupled to a processor (or processors) and computer-executable instructions embodied in the computer-storage media that, when executed by one or more computing devices, perform a method that perform any number of steps such as generating the dental implant management system and method as contemplated herein.

Various embodiments of the present disclosure can be implemented on an information processing system. The information processing system is capable of implementing and/or performing any of the functionality set forth above. Any suitably configured processing system can be used as the information processing system in embodiments of the present disclosure. The information processing system is operational with numerous other general purpose or special purpose computing system environments, networks, or configurations. Examples of well-known computing systems, environments, and/or configurations that may be suitable for use with the information processing system include, but are not limited to, personal computer systems, server computer systems, thin clients, hand-held or laptop devices, notebook computing devices, multiprocessor systems, mobile devices, microprocessor-based systems, set top boxes, programmable consumer electronics, network PCs, minicomputer systems, mainframe computer systems, Internet-enabled television, and distributed cloud computing environments that include any of the above systems or devices, and the like. As noted previously, the image processing can be any number of imaging processing techniques suited for the type of image capture device or sensor used in the embodiments which can include CT-Scans, X-Rays, MRIs, sonograms, high resolution still picture cameras or video, 3-D imaging system, or any other image capture device used in orthodontics, dentistry, or in medical settings generally.

For example, a user with a mobile device may be in communication with a server configured to implement the display system using the aforementioned elements, according to an embodiment of the present disclosure. The mobile device can be, for example, a multi-modal wireless communication device, such as a "smart" phone, configured to store and execute mobile device applications ("apps"). Such a wireless communication device communicates with a wireless voice or data network using suitable wireless communications protocols assuming the networks have the appropriate bandwidth to present real time images. Alternatively, the display system can be a computing and monitoring system with or without wireless communications as the case may be.

The display system may include, inter alia, various hardware components such as processing circuitry executing modules that may be described in the general context of computer system-executable instructions, such as program modules, being executed by the system. Generally, program modules can include routines, programs, objects, components, logic, data structures, and so on that perform particular tasks or implement particular abstract data types. The modules may be practiced in various computing environments such as conventional and distributed cloud computing environments where tasks are performed by remote processing devices that are linked through a communications network. In a distributed cloud computing environment, program modules may be located in both local and remote computer system storage media including memory storage devices. Program modules generally carry out the functions and/or methodologies of embodiments of the present disclosure, as described above.

In some embodiments, a system includes at least one memory and at least one processor of a computer system communicatively coupled to the at least one memory. The at least one processor can be configured to perform a method including methods described above.

According to yet another embodiment of the present disclosure, a computer readable storage medium comprises computer instructions which, responsive to being executed by one or more processors, cause the one or more processors to perform operations as described in the methods or systems above or elsewhere herein.

As shown in FIG. 12, an information processing system 101 of a system 200 can be communicatively coupled with the image processing module 150 and a group of client or other devices, or coupled to a presentation device for display at any location at a terminal or server location. According to this example, at least one processor 102, responsive to executing instructions 107, performs operations to communicate with the 3D image processing module 150 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the image processing module 150 and more generally used by the information processing system 200. The image processing module 150 can be coupled to one or more sensors 152 as needed. Such sensors can be CT-Scanning devices, X-Ray machines, panoramic X-Ray machines, cameras, video cameras, and other devices as contemplate herein. Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The image processing module 150, and the information processing system 200, can use the information from the history log such as in the analysis process and in making decisions related to a patient's treatment plan according to a database of best practices for a particular procedure or procedures.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 200 includes a user interface (or interfaces) 110 that comprises a user output interface 112 and user input interface 114. Examples of elements of the user output interface 112 can include a display, a speaker, one or more indicator lights, one or more transducers that generate audible indicators, and a haptic signal generator or any of the interfaces illustrated in FIGS. 1-7 or elsewhere in the application. Examples of elements of the user input interface 114 can include a keyboard, a keypad, a mouse, a track pad, a touch screen, a touch pad, a microphone that receives audio signals, a camera, a video camera, a CT-Scanner, or any other scanner that scans images. Some user inputs can be sensors or vice-versa. The received audio signals or scanned images, for example, can be converted to electronic digital representations and stored in memory, and optionally can be used with corresponding voice or image recognition software executed by the processor 102 to receive user input data and commands, or to receive test data for example. The voice recognition software can be used to enter or check off items on a checklist and further provide data or text entry allowing the practitioner to enter notes as needed.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can inter-communicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

FIGS. 1-8 illustrate examples of systems, methods or process flows, according to various embodiments of the present disclosure, which can operate in conjunction with the information processing system 200 of FIG. 12.

FIG. 13 illustrates a user interface 300 that allows a user to enter data such as blood pressure 302 and/or pulse and O2 levels 304. The user can do the measurements and data entry manually as a text entry or the software can cooperatively operate with monitoring devices that wirelessly provide and enter the data into the system automatically using Bluetooth or other wireless data protocol. A wired data connection can also be used in some embodiments.

FIG. 14 illustrates a user interface 400 enabling the entry of personal data related to a particular patient including medical conditions and allergies. For example, the hypothetical patient in this example can have high blood pressure and also be a smoker and corresponding check boxes 402 and 404 can be selected. Similarly, the patient can have allergies to penicillin and latex and check-boxes 406 and 408 can be selected. The Artificial Intelligence system will keep this data in mind for all aspects of the process including using such information for weighting risk assessments for particular procedures to ordering inventory for the patient that may be contraindicated (such as not ordering latex gloves or tape that might be used with or on the patient).

FIG. 15 illustrates an icon menu or interface 500 having a plurality of icons 502 representing different functions or data collections forming a part of the system. In one embodiment, the icons 602, 604, and 606 of interface 500 as shown in FIG. 16 indicate that data collection or measurements have been done by visually differentiating the icons 602, 604, and 606 from the other icons in the interface 500. Darkening or highlighting such icons can achieve this indication. A flashing icon or some other visual indicator can indicate that a measurement is out of a normal range. For example, icon 604 or 606 can automatically flash or highlight in red when the BP/PULSE/O2 measurements are out of range. The user would not be able to delete previous measurements but the icon will turn to its normal state again if the last measurements taken are within the normal range. Activating the icons in FIG. 15 or 16 will bring up a respective page or pop-up menu 700 as shown in FIG. 7 providing further details of the particular data entries. Activating the icon corresponding to medical conditions in FIG. 16 will provide the particular medical conditions 702 of smoking and high blood pressure as shown and the date of the initial visit and/or the date of the last visit or a complete record of any number of visits. Similarly, activating an icon corresponding to allergies in FIG. 16 will provide a respective page or pop-up menu 800 of the particular allergies 802 of penicillin and latex as shown in FIG. 18.

When activating or clicking on the BP/Pulse/O2 icon 606 of FIG. 16, the user can access the history of these measurements along with dates and times recorded as shown in the page or pop-up screen 900 of FIG. 19. If additional information is required such as normal range values or explanations for the parameters being measured, the circle-I icon 902 can be selected and another page 950 will provide such information as shown in FIG. 20.

Figure 21:
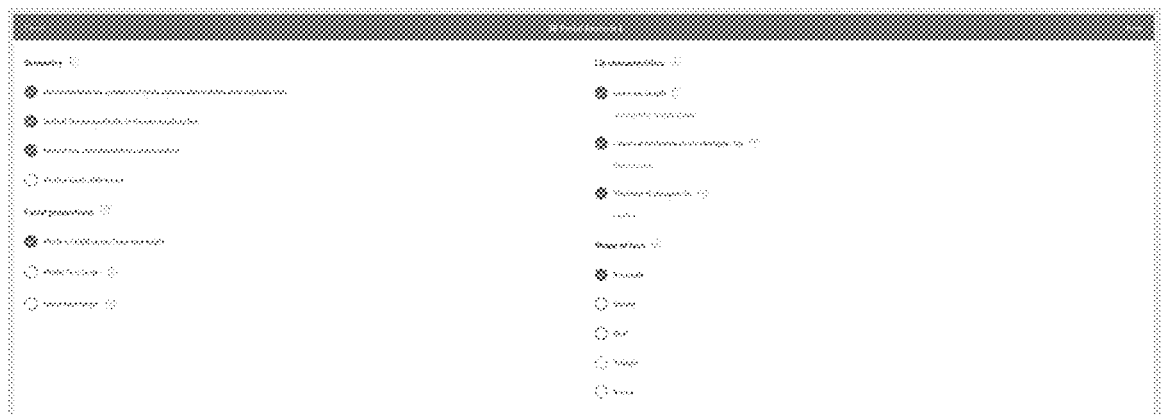
FIGS. 21-24 are a number of user interfaces enabling the entry of data for facial analysis, smile analysis and clinical findings in accordance with the embodiments.

Another aspect of the embodiments is the system's ability enter data for different aspects of the process including data entry for analysis and to further generate reports based on the data entered. The user interface 1001 of FIG. 21 illustrates various check-boxes that can be marked off by the user (e.g., the dental practitioner) for various aspects or parameters of a facial analysis such as symmetry, facial proportions, lip characteristics, and shape of face. Each of these aspects can have various choices as shown. The user interface 1002 of FIG. 22 includes further parameters that can be considered and checked off as appropriate. Some of the additional parameters can include facial profile type, nasolabial angle (lip support), vertical dimensions, and skeletal classification. As illustrated in prior figures, a circle-I icon can be included in the user interfaces 1001 and 1002 of FIGS. 21 and 22 to further explain the significance of the parameter and/or of the corresponding choices within a given parameter. For example, see "Skeletal Classification" and "Class 1" in FIG. 22.

Figure 22:
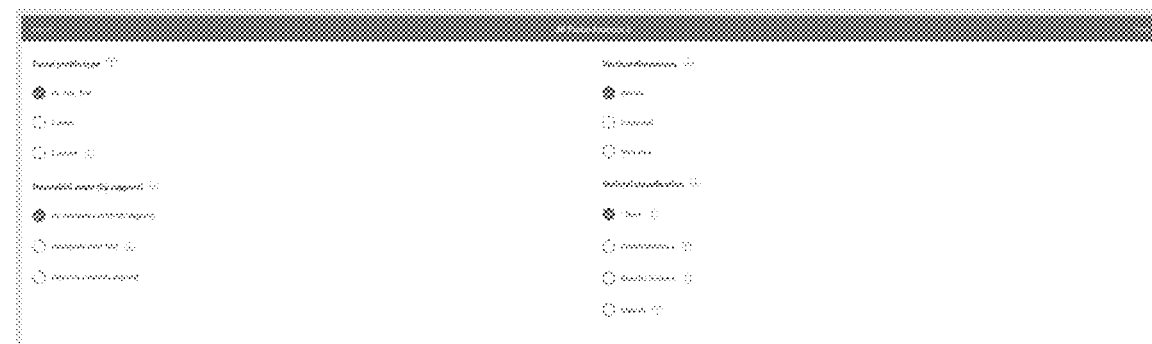
Figure 23:
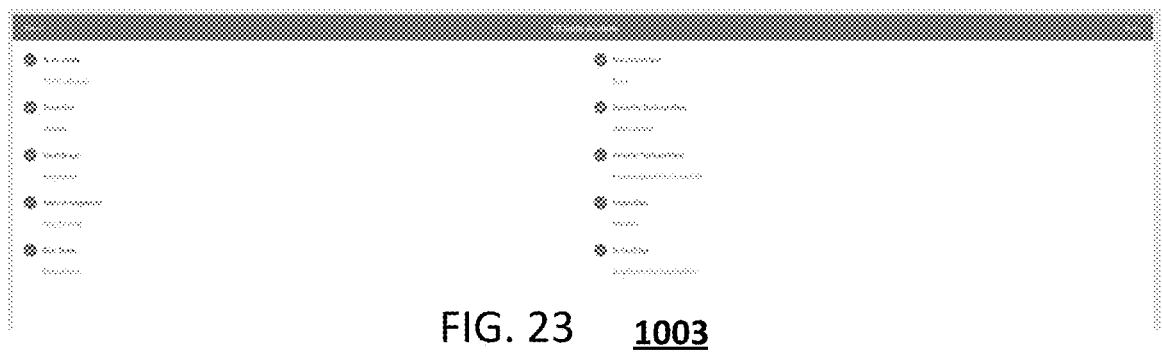
Figure 24:

Similar to FIGS. 21 and 22, the user interface 1003 of FIG. 23 illustrates various check-boxes that can be marked off by the user for various aspects or parameters of a smile analysis such as tooth shade, tooth size, tooth shape, tooth arrangement, gum shade, buccal corridor, posterior occlusal plane, anterior occlusal plane, incisal cant, and incisal edge. Each of these aspects can have various choices which are shown as already selected in FIG. 23. The user interface 1004 of FIG. 24 includes further parameters that can be considered and checked off as appropriate. Some of the additional parameters can include upper lip length, upper lip mobility, height of maxillary prosthesis, height of mandibular prosthesis, incisal edge to upper lip, and flanges needed. As illustrated in prior figures, a circle-I icon can be included in the user interfaces 1003 and 1004 of FIGS. 23 and 24 to further explain the significance of the parameter and/or of the corresponding choices within a given parameter. For example, see "Upper Mobility" in FIG. 24.

The user interfaces of FIGS. 21-24 can result or be generated from the selection of a block or square or step 2B called "Smile Design" that can be part of a second visit (refer similar blocks used in a consultation visit or a first visit as shown in FIG. 1). In one embodiment, when clicking or selecting the "Smile Design" a guide to collect 8 facial analysis data (FIGS. 21 and 22), 10 smile analysis data (FIG. 23), and 6 clinical data (FIG. 24) that all smile design related appear in one or more user interfaces or pages (4 pages used in the current example). As illustrated in the example, a total of 24 "checkpoints" can essentially provide a complete and comprehensive information gathering that enables a dental practitioner to decide what is the best prosthetic design for the patient. Upon completion of these 24 checkpoints as shown in the user interface 1005 of FIG. 25, the system offers in a user interface 1006 as shown in FIG. 26 to compile a report of the data and displays it at anytime desired in a format (such as PDF) to share with dental laboratory for a better smile design outcome.

Referring to the user interface 1007 of FIG. 27, another example report can be generated from the Evaluation and diagnostic report icon shown on the far right of the user interface 1007. This report can compile all data collected during the consultation visit, the data collection visit, and data analysis visit. An example of the smile analysis and design report 1008 is shown in FIG. 28. An example of the evaluation and diagnostic report 1009 is shown in FIG. 29. The embodiments are not limited to the reports and data shown in the examples provided. They are shown as representative of the types of reports and data that can be generated. Additionally, the system can provide options for customizing reports.

The invention claimed is:

1. A dental implant management system for a dental implant process for treatment from personal and diagnostic data collection to prosthesis delivery, comprising:

one or more computer storage mediums containing computer instructions and digitized patient records;

one or more processors operationally coupled to the one or more computer storage mediums, the computer instructions when executed by the one or more processors causes the one or more processors to perform the operations of:

presenting a user interface having a plurality of graphical elements representing tasks for completion, wherein a listing of the tasks is color coded for a status regarding each of the plurality of tasks;

presenting a plurality of guided checklists, within the user interface, for the dental implant process;

inputting values for personal and diagnostic data collection, within the user interface, for one or more of blood pressure, heart rate, blood oximetry, medical conditions, or allergies;

dynamically modifying at least one or more guided checklists among the plurality of guided checklists, within the user interface, using computer instructions and based on data entered, via one or more graphical elements of the user interface, to provide at least one dynamically modified guided checklist wherein the one or more processors further dynamically determines a further course of treatment recommendation based on a database of information as additional data is entered via one or more graphical elements of the user interface, wherein the computer instructions account for risk factors of general risk factors including poor bone density and reduced vertical distance between bone crest and opposing tooth, esthetic risk factors including thin gingiva and shape of interdental contact, functional risk factors including bruxism and type of diet, occlusal risk factors including presence of wear facets and direction of load and biomechanical risk factors including a connection to natural teeth and straight rather than tripod configuration, all of the risk factors collected as part of the diagnostic data collection; and dynamically updating and presenting the at least one dynamically modified guided checklist and the further course of treatment recommendation as part of the user interface as data is entered into the user interface to provide an improved user interface.

2. The dental implant management system of claim 1, wherein the one or more processors operationally coupled to the storage mediums are cloud based processors and wherein the dental implant management system further comprises a display coupled to the one or more processors for presenting the user interface and the at least one modified guided checklist and the further course of treatment recommendation.

3. The dental implant management system of claim 1, wherein the storage mediums are cloud based and the system is configured for a multi-user environment enabling a plurality of registered users to interact with the system.

4. The dental implant management system of claim 1, wherein the plurality of guided checklists dynamically modifies based on inputted values and a current status of the dental implant process.

5. The dental implant management system of claim 1, wherein the system further comprises an image capture device in the form of at least one of a CT-Scanner, an X-Ray machine, a magnetic resonance imaging machine, a sonogram machine, a high resolution still picture camera or, a 3-D imaging system that includes an image capture user interface that guides in a physical placement of the image capture device and further dynamically provides image correction.

6. The dental implant management system of claim 1, wherein the system uses a matrix based on rules and statistics that define input parameters to maximize correction results or reduce risk of harm to a patient.

7. The dental implant management system of claim 1, wherein the user interface further presents a divided calendar for patient visits including a consultation visit, a data collection visit, a data analysis visit, a surgical treatment visit, and a prosthodontics treatment visit.

8. The dental implant management system of claim 1, wherein the user interface further comprises a module for inputting a patient's personal profile information as part of the diagnostic data collection and wherein the general risk factors further include:

a very young age or a very old age, a compromised medical condition, a compromised psychological condition, high esthetic demands, limited availability for treatment and maintenance appointments, smoking habits, alcohol abuse, temporomandibular disorder, periodontal disease, etiology of edentulism, small jaw opening, poor hygiene, vestibular concavity or ridge dimensions, vertical bone resorption, mesiodistal dimensions of the edentulous space, acute lesions, chronic lesions distant from the prospective implant site, and bony lesions;

the esthetic risk factors further include: high maxillary gingival smile line, low mandibular gingival smile line, scalloped gingiva, papillae of adjacent teeth, form of natural teeth, the position of interdental contact, the vestibular concavity, the existence of adjacent implant, vertical bone resorption, proximal bony leaks, high esthetic requirements, or unstable provisional restoration;

the functional risk factors further include one or more factors of clenching, tongue thrusting, large tongue size, posterior position of planned implant, opposing arch, or optimal implant positioning;

occlusal risk factors further include one or more factors of unbalanced occlusion, posterior bite collapse, history of cracks and fractures of natural teeth, wide occlusal table, or lateral occlusal contact on the implant-supported prosthesis only; and biomechanical risk factors further include one or more factors of the number of implants possible or desired less than the number of roots replaces, a small implant diameter, a short implant, unsplinted implant crowns, excessive number or size of pontics, use of cantilever design, implants offset from center of the prosthesis, excessively high restoration, unsatisfactory primary implant stability, lack of passive prosthetic fit, pier abutment, mandibular flexion, or immediate loading.

9. The dental implant management system of claim 1, wherein the user interface further comprises a module for obtaining digitized imaging information selected among one or more of computer tomography images, photographs, video, x-rays, or magnetic resonance imaging.

10. The dental implant management system of claim 1, wherein the user interface further comprises a module for obtaining a patient's consent and other acknowledgements.

11. The dental implant management system of claim 1, wherein the user interface further comprises a module for obtaining dental impressions.

12. The dental implant management system of claim 1, wherein the user interface further comprises a module for coordinating lab orders and maintaining inventory for materials used in a dental implant process and the computer instructions further use data from lab orders and maintaining inventory for materials for weighting risk assessments for particular procedures that are contraindicated.

13. The dental implant management system of claim 1, further comprising a camera operationally coupled to one or more processors, wherein the one or more processors are configured to guide and take pre-set images based on a desired smile profile.

14. A client device for a dental implant management system for a dental implant process for treatment from personal and diagnostic data collection to prosthesis delivery, comprising:

one or more computer storage mediums containing computer instructions enabling secure access to digitized patient records;

one or more processors operationally coupled to the one or more computer storage mediums, the computer instructions when executed by the one or more processors causes the one or more processors to perform the operations of:

presenting a user interface having a plurality of graphical elements representing tasks for completion, wherein a listing of the tasks is color coded for a status regarding each task of the plurality of tasks;

presenting a plurality of guided checklists, within the user interface, for the dental implant process;

receiving input values for personal and diagnostic data collection, within the user interface, for one or more of blood pressure, heart rate, blood oximetry, medical conditions, or allergies;

dynamically modifying one or more guided checklists among the plurality of guided checklists, within the user interface, using computer instructions based on data entered, via one or more graphical elements of the user interface, to provide at least one dynamically modified guided checklist wherein the one or more processors further dynamically determines a further course of treatment recommendation based on a database of information as additional data is entered via one or more graphical elements of the user interface, wherein the computer instructions account for risk factors of general risk factors including poor bone density and reduced vertical distance between bone crest and opposing tooth, esthetic risk factors including thin gingiva and shape of interdental contact, and biomechanical risk factors including a connection to natural teeth and straight rather than tripod configuration; and dynamically updating and presenting the at least one modified guided checklist and the further course of treatment recommendation as part of the user interface as data is entered into the user interface system to provide an improved user interface.

15. The client device of claim 14, wherein the one or more storage mediums are operationally coupled to remote storage mediums and processors enabling remote storage and processing of data and further configured for a multi-user environment enabling a plurality of registered users to interact with the system.

16. The client device of claim 14, wherein the client device further comprises an image capture device that includes an image capture user interface that guides in a physical placement of the image capture device and client device and further dynamically provides image correction.

17. The client device of claim 14, wherein the user interface further comprises a module for obtaining either locally or remotely digitized imaging information selected among magnetic resonance imaging and one or more of computer tomography images, photographs, video, or x-rays.

18. The client device of claim 14, wherein the user interface further comprises a module for obtaining a patient's consent and other acknowledgements on a touch screen or on a biometric input device indicative of a patient's consent.

19. The client device of claim 14, wherein the computer instructions further use data from lab orders and maintaining inventory for materials for weighting risk assessments for particular procedures that are contraindicated.

20. A method of managing a dental implant process for treatment, comprising:

maintaining a plurality of digitized patient records using one or more computer storage mediums containing computer instructions;

presenting a user interface on a client device providing for a plurality of graphical elements representing tasks for completion, wherein a listing of the tasks is color coded for a status regarding each task of the plurality of tasks;

receiving a plurality of inputs for personal and diagnostic data collection, within the user interface, for a dental implant patient;

presenting a plurality of guided checklists for the dental implant process that dynamically changes, within the user interface, based on the plurality of inputs and the status regarding each task of the plurality of tasks;

using computer instructions to dynamically modify one or more guided checklists among the plurality of guided checklists, within the user interface, based on the plurality of inputs and the status regarding each task of the plurality of tasks to provide at least one dynamically modified guided checklist wherein at least one processor further dynamically determines a further course of treatment recommendation based on a database of information as additional data is entered via one or more graphical elements of the user interface, wherein the computer instructions account for the plurality of inputs for personal and diagnostic data collection for risk factors of general risk factors including poor bone density and reduced vertical distance between bone crest and opposing tooth and biomechanical risk factors including a connection to natural teeth and straight rather than tripod configuration, all collected as part of the plurality of inputs for personal and diagnostic data collection; and dynamically updating and presenting the at least one dynamically modified guided checklist and the further course of treatment recommendation as part of the user interface as the at least one dynamically modified guided checklist is dynamically modified to provide an improved user interface.

* * * * *